US010352936B2

(12) United States Patent
Modiano et al.

(10) Patent No.: US 10,352,936 B2
(45) Date of Patent: Jul. 16, 2019

(54) USE OF TUMOR FAS EXPRESSION TO DETERMINE RESPONSE TO ANTI-CANCER THERAPY

(75) Inventors: Jaime Modiano, Roseville, MN (US); Donald Bellgrau, Highlands Ranch, CO (US); Richard C. Duke, Denver, CO (US)

(73) Assignee: ApopLogic Pharmaceuticals, Inc., Aurora, CO (US)

( * ) Notice: Subject to any disclaimer, the term of this patent is extended or adjusted under 35 U.S.C. 154(b) by 501 days.

(21) Appl. No.: 14/111,448

(22) PCT Filed: Apr. 13, 2012

(86) PCT No.: PCT/US2012/033681
§ 371 (c)(1),
(2), (4) Date: Feb. 5, 2014

(87) PCT Pub. No.: WO2012/142526
PCT Pub. Date: Oct. 18, 2012

(65) Prior Publication Data
US 2014/0294754 A1    Oct. 2, 2014

Related U.S. Application Data

(60) Provisional application No. 61/475,468, filed on Apr. 14, 2011.

(51) Int. Cl.
*A01N 63/00* (2006.01)
*A61K 48/00* (2006.01)
*G01N 33/574* (2006.01)
*C12Q 1/6886* (2018.01)
*C12Q 1/6888* (2018.01)
*G01N 33/68* (2006.01)
*A61K 38/17* (2006.01)
*A61K 38/19* (2006.01)

(52) U.S. Cl.
CPC ..... *G01N 33/57492* (2013.01); *A61K 38/177* (2013.01); *A61K 38/191* (2013.01); *C12Q 1/6886* (2013.01); *C12Q 1/6888* (2013.01); *G01N 33/57407* (2013.01); *G01N 33/6863* (2013.01); *C12Q 2600/106* (2013.01); *G01N 2333/7151* (2013.01); *G01N 2800/52* (2013.01)

(58) Field of Classification Search
CPC ....... A61K 39/00; A61K 38/17; A61K 38/177
USPC ...................................... 424/93.2
See application file for complete search history.

(56) References Cited

U.S. PATENT DOCUMENTS

| | | | |
|---|---|---|---|
| 4,708,871 A | 11/1987 | Geysen | |
| 4,797,368 A | 1/1989 | Carter et al. | |
| 4,833,092 A | 5/1989 | Geysen | |
| 5,139,941 A | 8/1992 | Muzyczka et al. | |
| 5,223,409 A | 6/1993 | Ladner et al. | |
| 5,403,484 A | 4/1995 | Ladner et al. | |
| 5,556,762 A | 9/1996 | Pinilla et al. | |
| 5,571,689 A | 11/1996 | Heuckeroth et al. | |
| 5,663,143 A | 9/1997 | Ley et al. | |
| 5,750,373 A | 5/1998 | Garrard et al. | |
| 5,759,536 A | 6/1998 | Bellgrau et al. | |
| 6,325,999 B1 | 12/2001 | Bellgrau et al. | |
| 6,566,118 B1 | 5/2003 | Atkinson et al. | |
| 6,596,535 B1 | 7/2003 | Carter | |
| 6,989,264 B2 | 1/2006 | Atkinson et al. | |
| 6,995,006 B2 | 2/2006 | Atkinson et al. | |
| 8,715,645 B2 | 5/2014 | Bellgrau et al. | |
| 2003/0157502 A1 | 8/2003 | Krammer et al. | |

FOREIGN PATENT DOCUMENTS

| | | |
|---|---|---|
| EP | 0 488 528 B1 | 6/1992 |
| WO | WO-84/03506 A1 | 9/1984 |
| WO | WO-84/03564 A1 | 9/1984 |
| WO | WO-91/18088 A1 | 11/1991 |
| WO | WO-93/09239 A1 | 5/1993 |
| WO | WO 9903998 A1 * | 1/1999 |
| WO | WO-99/11764 A2 | 3/1999 |
| WO | WO-99/11764 A3 | 3/1999 |
| WO | WO 9920308 A1 * | 4/1999 |
| WO | WO-00/00823 A1 | 1/2000 |
| WO | WO-00/39585 A1 | 7/2000 |
| WO | WO-2005/123141 A2 | 12/2005 |
| WO | WO-2005/123141 A3 | 12/2005 |
| WO | WO-2006/073496 A2 | 7/2006 |
| WO | WO-2006/073496 A3 | 7/2006 |
| WO | WO-2008/008155 A2 | 1/2008 |
| WO | WO-2008/008155 A3 | 1/2008 |

OTHER PUBLICATIONS

Eisele (online Dec. 22, 2010; Neuro-Oncology, 13:155-164).*
Hedlund (1999, Cell death and differentiation, 6:175-182).*
Arai (1997, PNAS, 94:13862-13867).*
Gordon (2009, The Role of Fas/FasL in the Metastatic Potential of Osteosarcoma and Targeting this Pathway for the Treatment of Osteosarcoma Lung Metastases. In: Jaffe N., Bruland O., Bielack S. (eds) Pediatric and Adolescent Osteosarcoma. Cancer Treatment and Research, vol. 152. Springer, Boston, MA).*
Ryan (Cancer Res, 2005, 65:9817-9823).*
Alizadeh, A.A. et al. (Feb. 3, 2000). "Distinct Types of Diffuse Large B-Cell Lymphoma Identified by Gene Expression Profiling," *Nature* 403(6769):503-511.
Asensio, C. et al. (Nov.-Dec. 2007). "Fas Expression is Associated with a Better Prognosis in Laryngeal Squamous Cell Carcinoma," *Anticancer Research* 27(6B):4083-4086.

(Continued)

*Primary Examiner* — Valarie E Bertoglio
(74) *Attorney, Agent, or Firm* — Morrison & Foerster LLP

(57) ABSTRACT

The invention provides methods for using expression levels of Fas to select individuals or subpopulation of individuals who can benefit from an anti-cancer therapy and for assessing whether an individual suspected of having or developing cancerous tumors will beneficially respond to an anticancer therapy. The invention additionally provides methods of treatment for individuals selected as likely to benefit from anti-cancer therapy based on Fas expression levels.

4 Claims, 8 Drawing Sheets

(56) References Cited

OTHER PUBLICATIONS

Blacklow, N.R. (1988). "Adeno-Associated Viruses of Humans," Chapter 11 in *Parvoviruses and Human Disease*, J.R. Pattison, ed., CRC Press, Inc., pp. 165-174.
Bowles, D.E. et al. (2006). "The Genus *Dependovirus*," in *Parvoviruses*, Kerr, J.R. et al. eds., Hudder Arnold, London, UK, pp. 15-23.
Clackson, T. et al. (Aug. 15, 1991). "Making Antibody Fragments Using Phage Display Libraries," *Nature* 352(6336):624-628.
Cwirla, S.E. et al. (Aug. 1990). "Peptides on Phage: A Vast Library of Peptides for Identifying Ligands," *PNAS* 87(16):6378-6382.
Geysen, H.M. et al. (Jul. 1984). "Use of Peptide Synthesis to Probe Viral Antigens for Epitopes to a Resolution of a Single Amino Acid," *PNAS* 81(13):3998-4002.
Geysen, H.M. et al. (Jan. 1985). "Small Peptides Induce Antibodies with a Sequence and Structural Requirement for Binding Antigen Comparable to Antibodies Raised Against the Native Protein," *PNAS* 82(1):178-182.
Geysen, H.M. et al. (1986). "The Delineation of Peptides Able to Mimic Assembled Epitopes," *Ciba Found Symp.* 119:130-149.
Geysen, H.M. et al. (Sep. 24, 1987). "Strategies for Epitope Analysis Using Peptide Synthesis," *J. Immunol. Meth.* 102(2):259-274.
Heid, C.A. et al. (Oct. 1996). "Real Time Quantitative PCR," *Genome Research* 6(10):986-994.
Kang, A.S. et al. (May 15, 1991). "Linkage of Recognition and Replication Functions by Assembling Combinatorial Antibody Fab Libraries Along Phage Surfaces," *PNAS* 88(10):4363-4366.
Koomägi, R. et al. (Jun. 21, 1999). "Expression of Fas (CD95/Apo-1) and Fas Ligand in Lung Cancer, Its Prognostic and Predictive Relevance," *International Journal of Cancer* 84(3):239-243.
Lowman, H.B. et al. (Nov. 12, 1991). "Selecting High-Affinity Binding Proteins by Monovalent Phage Display," *Biochemistry* 30(45):10832-10838.
Mao, H. et al. (Dec. 15, 2007; e-pub. Oct. 1, 2007). "Effects of Specific Antisense Oligonucleotide Inhibition of Fas Expression on T Cell Apoptosis Induced by Fas Ligand," *Int. Immunopharmacology* 7 (13):1714-1722.
Marks, J.D. et al. (Dec. 5, 1991). "By-Passing Immunization. Human Antibodies from V-Gene Libraries Displayed on Phage," *J. Mol. Biol.* 222(3):581-597.
Reimer, T. et al. (2002; e-published on Jun. 21, 2002). "Tournour Fas Ligand: Fas Ration Greater Than 1 is an Independent Marker of Relative Resistance to Tamozifen Therapy in Hormone Receptor Positive Breast Cancer," *Breast Cancer Research* 4(5):R9, eight pages.
Rose, J.A. (1974). "Parvovirus Reproduction," Chapter 1 in *Comprehensive Virology* H. Fraenkel-Conrat, ed. et al., Plenum Press, New York, 3:1-61.
Sawchuk, S.J. et al. (Mar. 1, 1996). "Anti-T Cell Receptor Monoclonal Antibody Prolongs Transgene Expression Following Adenovirus-Mediated In Vivo Gene Transfer to Mouse Synovium," *Hum. Gene Ther.* 7(4):499-506.
Schoofs, P.G. et al. (Jan. 15, 1988). "Epitopes of an Influenza Viral Peptide Recognized by Antibody at Single Amino Acid Resolution," *J. Immunol.* 140(2):611-616.
Scott, M.C. et al. (Sep. 2011). "Molecular Subtypes of Osteosarcoma Identified by Reducing Tumor Heterogeneity Through an Interspecies Comparative Approach," *Bone* 49(3):356-367.
Shibakita, M. et al. (Sep. 1999). "Prognostic Significance of Fas and Fas Ligand Expressions in Human Esophageal Cancer," *Clinical Cancer Research* 5(9):2464-2469.
Smith, G.P. (Oct. 1991). "Surface Presentation of Protein Epitopes Using Bacteriophage Expression Systems," *Current Opin. Biotechnol.* 2(5):668-673.
Tattersall, P. (2006). "The Evolution of Parvovirus Taxonomy," in *Parvoviruses*, Kerr, J.R. et al. eds., Hudder Arnold, London, UK, pp. 5-14.
Thomas, R. et al. (2003). "A Canine Cancer-Gene Microarray for CGH Analysis of Tumors," *Cytogenet. Genome Res.* 102(1-4):254-260.
Thomas, R. et al. (Dec. 2005). "Construction of a 2-Mb Resolution BAC Microarray for CGH Analysis of Canine Tumors," *Genome Res.* 15(12):1831-1837.
Tsujii, H. et al. (Aug. 2010; e-pub. Apr. 26, 2010). "Screening of Cell Death Genes with a Mammalian Genome-Wide RNAi Library," *J. Biochem.* 148(2):157-170.
International Search Report and Written Opinion of the International Searching Authority dated Aug. 15, 2012 for PCT Application No. PCT/US2012/033681, filed on Apr. 13, 2012, sixteen pages.
U.S. Appl. No. 14/218,755, filed Mar. 18, 2014, by Bellgrau et al.

\* cited by examiner

A.

B.

C.

A.

B.

C.

A.

B.

A.

B.

USE OF TUMOR FAS EXPRESSION TO DETERMINE RESPONSE TO ANTI-CANCER THERAPY

CROSS-REFERENCE TO RELATED APPLICATIONS

This application is a National Phase application under 35 U.S.C. § 371 of International Application No. PCT/US2012/033681, filed Apr. 13, 2012 and claims priority to U.S. Provisional Application No. 61/475,468, filed Apr. 14, 2011, the disclosures of which are incorporated by reference herein in their entirety.

STATEMENT OF FEDERALLY FUNDED RESEARCH

This invention was made with U.S. Government support under grant number 1R43 CA119840-01A1 awarded by the United States National Institutes of Health. The United States government has certain rights in this invention.

FIELD OF THE INVENTION

The invention provides methods for using expression levels of Fas to select individuals who will benefit from an anti-cancer therapy and for assessing whether an individual suspected of having or developing cancerous tumors will beneficially respond to an anticancer therapy as well as methods of treatment using the same. The invention also provides compositions and methods for treating individuals suspected of having or developing cancerous tumors.

BACKGROUND OF THE INVENTION

Cancers in the form of malignant tumors are the second leading cause of death in the United States after heart disease (U.S. Dept. of Health and Human Services, *National Vital Statistics Reports*, 58(19), May 20, 2010). Many cancers are characterized by an increase in the number of neoplastic cells originating from an initially normal tissue which subsequently propagate to form a tumor mass. With malignant tumors, neoplastic cells invade neighboring tissues ultimately leading to their spread via the blood or lymphatic system to lymph nodes and other locations distant from the site of the original tumor via a process called metastasis. Cancer manifests itself in a wide variety of forms, with each form characterized by varied degrees of invasiveness and aggressiveness.

Apoptosis is the regulated process of programmed cell death (PCD) which occurs in multicellular organisms. In response to certain external or internal cellular signaling events, cells undergo apoptosis which eventually leads to characteristic changes in cell morphology and cellular death. Normally, apoptosis is necessary for the function and development of multicellular organisms. In some cases, however, loss of apoptotic control can lead to a variety of diseases and conditions, including cancer. Over the past several years, many molecular pathways which modulate a cell's ability to control apoptotic processes have been identified. One such pathway is the Fas/Fas Ligand system.

Fas Ligand (a.k.a. FasL or CD95L) is a type-II transmembrane protein member of the tumor necrosis factor (TNF) superfamily. Binding of FasL to its receptor, known as Fas (a.k.a. CD95, Apo-1, and tumor necrosis factor receptor superfamily, member 6 (TNFRSf6)), induces apoptosis in those cells expressing Fas on their plasma membranes. Over the past two decades, the Fas/FasL system has been used to try to understand the role of apoptosis in cancers as well as to attempt to use components of the system to treat a number of proliferative diseases (See, e.g., Takahashi et al, *International Immunology*, 6(10):1567-74 (1994); Nagata et al., *Science*, 267:1449-1456 (1995); Takahashi et al., *Cell*, 66:969-976 (1994); Lee et al., *FASEB J.*, 8(5):A770 (1994); Suda et al., *Cell*, 75:1169-78 (1993); Suda et al., *Journal of Experimental Medicine*, 179:873-879 (1994)). U.S. Patent Application Publication No. 2004/0224389 describes constructs encoding FasL and other apoptosis-inducing proteins, which were capable of inducing apoptosis in a desired target cell.

In some cases, biomarkers are gene expression products measured in blood or within a particular cell type whose concentration, existence, or lack thereof reflects the severity or presence of some disease state. In attempts to discover effective biomarkers for cancer diagnosis and therapy, researchers have sought to identify targets that are differentially expressed in cancer cells as compared to expression in or on one or more types of normal non-malignant cells. In some cases, identification of such tumor-associated biomarkers has given rise to the ability to specifically target cancer cells for destruction based on the differential relative expression of one or more particular biomarkers either within a cancer cell or expressed on its surface. However, complicating this strategy is the fact that, even within tumors originating from the same tissue type, substantial variation in gene expression patterns may exist between individuals or between subpopulations of individuals suffering from the same type of cancer. The advent of genome-wide gene expression profiling has permitted the molecular characterization of intertumoral gene expression variability, revealing molecular signatures that reflect underlying pathogenic mechanisms and molecular features that may be associated with survival in individual subtypes of tumors (Alizedeh et al, *Nature*, 403:503-511 (2000)). Identification of tumor subtypes is critical, as anti-cancer therapies that may be effective for the treatment of one subtype may not be similarly effective in treating other subtypes due to the consequences of variation in gene expression patterns.

Consequently, given the unreliability of individual gene expression within tumors of the same cancer type, there exists a need for a biomarker whose measurement can not only predict the likelihood that an individual with a particular tumor subtype will benefit from anti-cancer therapies, but whose expression is also useful for selecting individuals or subpopulations of individuals for a particular anti-cancer therapy. Such a diagnostic marker would be helpful for guiding health care professionals involved in the treatment of an individual suffering from particular subtypes of malignant tumors originating from the same tissue. A diagnostic marker of this sort would also be useful to track prognosis following the initiation of treatment.

This invention provides such a biomarker and uses the expression level of Fas within a tumor to select individuals or subpopulations of individuals who will benefit from an anti-cancer therapy.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provided herein discloses, inter alia, methods for using the expression level of a single biomarker, Fas, to select individuals or subpopulations of individuals suspected of having or developing cancer that will benefit from particular anti-cancer therapies, methods for using Fas expression levels of a tumor to guide the treatment of individuals having or suspected of developing cancerous tumors, and methods for treating individuals or subpopulations of individuals suspected of having or developing cancer.

Accordingly, in one aspect, there is provided a method for treating an individual suspected of having or developing cancerous tumors comprising administering an effective amount of a composition comprising FasL to the tumor, wherein the individual has low Fas expression in the cells of the cancerous tumor. In some aspects, the method further comprises administering an effective amount of an additional anti-cancer therapy to the individual. In other aspects, administering an effective amount of a composition comprising FasL to the tumor promotes inflammation in the tumor and surrounding tissue. In some aspects, there is provided a method of treating an individual suspected of having or developing cancerous tumors, the method comprising selecting an individual who would benefit from anti-cancer treatment based on low Fas expression in the tumor cells from the individual and administering a composition comprising FasL to the tumor. In some aspects, low Fas expression comprises low Fas mRNA expression or low Fas protein expression. In other aspects, the composition comprising FasL is an adenoviral vector expressing FasL (e.g., Fasaret™). In other aspects, the method further comprises administering an additional anti-cancer therapy to the individual. In another aspect, administering a composition comprising FasL to the tumor promotes inflammation in the tumor and surrounding tissue. In other aspects, inflammation in the tumor comprises increased necrosis, apoptosis, and/or fibrosis. In yet another aspect, inflammation in the tumor comprises increased white blood cell infiltration into the tumor. In some aspects, the white blood cells initially comprise neutrophils following administration of a composition comprising FasL to the tumor. In other aspects, the white blood cells comprise lymphocytes and in another aspect the white blood cells comprise CD3+ cells. In other aspects, the individual is diagnosed with cancer. In other aspects, the individual has cancer. In another aspect, the cancer is naturally occurring. In other aspects the cancer is induced while in still other aspects the cancer is induced due to exposure to carcinogens or other environmental toxins. In some aspects, the individual is a human. In other aspects, the individual is a non-human mammal. In other aspects, the individual is a dog. In some aspects, the amount of Fas expression is determined by measuring the amount of Fas mRNA. In some aspects, the amount of Fas expression is determined by RT-PCR or another PCR-based method, Northern Blot or SAGE. In some aspects, the amount of Fas expression is determined by qRT-PCR. In some aspects, the amount of Fas expression is determined by measuring the amount of Fas protein. In some aspects, the amount of Fas expression is determined by immunohistochemistry, ELISA, RIA, Western or immunoblot, or another antibody-based method. In some aspects, the amount of Fas expression is determined by flow cytometry.

In another aspect, provided herein are methods for treating an individual suspected of having or developing cancerous tumors, the method comprising: (a) administering an effective amount of a composition which blocks the interaction between FasL and Fas to the tumor, wherein the composition blocks the interaction between FasL and Fas but does not cause Fas-mediated programmed cell death; and (b) administering a composition comprising an effective amount of FasL to the tumor, wherein the individual has high Fas expression in the cells of the cancerous tumor. In some aspects, the composition comprising FasL is an adenoviral vector expressing FasL. In some aspects, the method further comprises administering an effective amount of an additional anti-cancer therapy to the individual. In another aspect, there is provided a method of treating an individual suspected of having or developing cancerous tumors comprising (a) selecting an individual who would benefit from anti-cancer treatment based on high Fas expression in the tumor cells from the individual, (b) administering a composition which blocks the interaction between FasL and Fas to the tumor, wherein the composition which blocks the interaction between FasL and Fas does not cause Fas-mediated programmed cell death, and (c) administering a composition comprising FasL to the tumor. In some aspects, high Fas expression comprises high Fas mRNA expression or high Fas protein expression. In some aspects, sequentially administering the compositions in steps (b) and (c) to the tumor promotes inflammation in the tumor and surrounding tissue. In other aspects, the composition comprising FasL is an adenoviral vector expressing FasL (e.g., Fasaret™). In other aspects, the method further comprises administering an additional anti-cancer therapy to the individual. In other aspects, inflammation in the tumor comprises increased necrosis, apoptosis, and/or fibrosis. In yet another aspect, inflammation in the tumor comprises increased white blood cell infiltration into the tumor. In some aspects, the white blood cells initially comprise neutrophils following administration of a composition comprising FasL to the tumor. In other aspects, the white blood cells comprise lymphocytes and in another aspect the white blood cells comprise CD3+ cells. In other aspects, the composition which blocks the interaction between FasL and Fas comprises a Fas antibody. In some aspects, the individual is a human. In other aspects, the individual is a non-human mammal. In other aspects, the individual is a dog. In other aspects, the individual is diagnosed with cancer. In other aspects, the individual has cancer. In some aspects, the amount of Fas expression is determined by measuring the amount of Fas mRNA. In some aspects, the amount of Fas expression is determined by RT-PCR or another PCR-based method, Northern Blot or SAGE. In some aspects, the amount of Fas expression is determined by qRT-PCR. In some aspects, the amount of Fas expression is determined by measuring the amount of Fas protein. In some aspects, the amount of Fas expression is determined by immunohistochemistry, ELISA, RIA, Western or immunoblot, or another antibody-based method. In some aspects, the amount of Fas expression is determined by flow cytometry.

In some aspects, there is provided a method for inducing a localized inflammatory effect in an individual suspected of having or developing cancerous tumors comprising administering a composition comprising an effective amount of FasL to the tumor, wherein the individual has low Fas expression in the cells of the cancerous tumor. In some aspects, the method further comprises administering an effective amount of an additional anti-cancer therapy to the individual. In other aspects, administering a composition comprising an effective amount of FasL to the tumor promotes inflammation in the tumor and surrounding tissue. In another aspect, there is provided a method for inducing a localized inflammatory effect in an individual suspected of having or developing cancerous tumors, the method comprising selecting an individual who would benefit from anti-cancer treatment based on low Fas expression in the tumor cells from the individual and administering a composition comprising FasL to the tumor. In some aspects, low Fas expression comprises low Fas mRNA expression or low Fas protein expression. In other aspects, the composition comprising FasL is an adenoviral vector expressing FasL (e.g., Fasaret™). In other aspects, the method further comprises administering an additional anti-cancer therapy to the individual. In another aspect, administering a composition comprising FasL to the tumor promotes inflammation in the tumor and surrounding tissue. In other aspects, inflammation in the tumor comprises increased necrosis, apoptosis, and/or fibrosis. In yet another aspect, inflammation in the tumor comprises increased white blood cell infiltration into the tumor. In some aspects, the white blood cells initially comprise neutrophils following administration of a composition comprising FasL to the tumor. In other aspects, the white blood cells comprise lymphocytes and in another aspect the white blood cells comprise CD3+ cells. In other aspects, the individual is diagnosed with cancer. In other aspects, the individual has cancer. In another aspect, the cancer is naturally occurring. In other aspects the cancer is induced while in still other aspects the cancer is induced due to exposure to carcinogens or other environmental toxins. In some aspects, the individual is a human. In other aspects, the individual is a non-human mammal. In other aspects, the individual is a dog. In some aspects, the amount of Fas expression is determined by measuring the amount of Fas mRNA. In some aspects, the amount of Fas expression is determined by RT-PCR or another PCR-based method, Northern Blot or SAGE. In some aspects, the amount of Fas expression is determined by qRT-PCR. In some aspects, the amount of Fas expression is determined by measuring the amount of Fas protein. In some aspects, the amount of Fas expression is determined by immunohistochemistry, ELISA, RIA, Western or immunoblot, or another antibody-based method. In some aspects, the amount of Fas expression is determined by flow cytometry.

In some aspects, the invention provides a method of assessing a likelihood of a beneficial response to an anti-cancer therapy in an individual suspected of having or developing cancerous tumors comprising determining the amount of Fas expression in a biological sample from the tumor and determining the likelihood of a beneficial response to an anti-cancer therapy, wherein the beneficial response is indicated by low and/or decreased Fas expression in the sample. In one aspect, the biological sample can be from a solid tumor, including a subcutaneously accessible tumor. Examples of solid tumors include sarcoma, melanoma, prostate cancer, glioma, urothelial cancer, head and neck cancers, and colorectal cancer. In another aspect, the biological sample can be fixed, paraffin embedded, fresh, or frozen. In one aspect, the biological sample can be obtained by needle or core biopsy or by fine needle aspiration. In some aspects, decreased Fas expression comprises decreased Fas mRNA expression or decreased Fas protein expression. In other aspects, the amount of Fas expression is determined by measuring the amount of Fas mRNA. In another aspect, the amount of Fas expression is determined by RT-PCR or another PCR-based method, Northern Blot or SAGE. In yet another aspect, the amount of Fas expression is determined by qRT-PCR. In some aspects, the amount of Fas expression is determined by measuring the amount of Fas protein. In some aspects, the amount of Fas expression is determined by immunohistochemistry, ELISA, RIA, Western or immunoblot, or another antibody-based method. In other aspects, the amount of Fas expression is determined by flow cytometry. In some aspects, the individual is a human. In other aspects, the individual is a non-human mammal. In other aspects, the individual is a dog. In other aspects, the individual is diagnosed with cancer. In other aspects, the individual has cancer. In some aspects, the method further comprises providing the assessment of the likelihood of a beneficial response to an anti-cancer therapy to a health care professional who is involved in determining the course of treatment for the individual. In another aspect, the assessment of the likelihood of a beneficial response to an anti-cancer therapy is recorded on a fixed medium.

In another aspect, there is provided a method of selecting an individual who will benefit from anti-cancer therapy comprising determining the amount of Fas expression in a biological sample from a tumor and identifying the individual who will benefit from anti-cancer therapy, when the amount of Fas expression in the sample is low. In one aspect, the biological sample can be from a solid tumor, including a subcutaneously accessible tumor. Examples of solid tumors include sarcoma, melanoma, prostate cancer, glioma, urothelial cancer, head and neck cancers, and colorectal cancer. In another aspect, the biological sample can be fixed, paraffin embedded, fresh, or frozen. In one aspect, the biological sample can be obtained by needle or core biopsy or fine needle aspiration. In some aspects, low Fas expression comprises decreased Fas mRNA expression or decreased Fas protein expression. In other aspects, the amount of Fas expression is determined by measuring the amount of Fas mRNA. In another aspect, the amount of Fas expression is determined by RT-PCR or another PCR-based method, Northern Blot or SAGE. In yet another aspect, the amount of Fas expression is determined by qRT-PCR. In some aspects, the amount of Fas expression is determined by measuring the amount of Fas protein. In some aspects, the amount of Fas expression is determined by immunohistochemistry, ELISA, RIA, Western or immunoblot, or another antibody-based method. In other aspects, the amount of Fas expression is determined by flow cytometry. In some aspects, the individual is a human. In other aspects, the individual is a non-human mammal. In other aspects, the individual is a dog. In other aspects, the individual is diagnosed with cancer. In other aspects, the individual has cancer. In some aspects, the method further comprises providing the selection to a health care professional who is involved in determining the course of treatment for the individual. In another aspect, the selection is recorded on a fixed medium.

In another aspect, there is provided a method of determining the likelihood of long-term survival in an individual suspected of having or developing cancerous tumors comprising determining the amount of Fas expression in a biological sample from the individual and determining the likelihood of long-term survival, wherein the likelihood of long-term survival is indicated by decreased Fas expression in the sample from the individual. In one aspect, the biological sample can be from a solid tumor, including a subcutaneously accessible tumor. Examples of solid tumors include sarcoma, melanoma, prostate cancer, glioma, urothelial cancer, head and neck cancers, and colorectal cancer. In another aspect, the biological sample can be fixed, paraffin embedded, fresh, or frozen. In one aspect, the biological sample can be obtained by needle or a core biopsy or fine needle aspiration. In some aspects, decreased Fas expression comprises decreased Fas mRNA expression or decreased Fas protein expression. In other aspects, the amount of Fas expression is determined by measuring the amount of Fas mRNA. In another aspect, the amount of Fas expression is determined by RT-PCR or another PCR-based method, Northern Blot or SAGE. In yet another aspect, the amount of Fas expression is determined by qRT-PCR. In some aspects, the amount of Fas expression is determined by measuring the amount of Fas protein. In some aspects, the amount of Fas expression is determined by immunohistochemistry, ELISA, RIA, Western or immunoblot, or another antibody-based method while in other aspects. In other aspects, the amount of Fas expression is determined by flow cytometry. In some aspects, the individual is a human. In other aspects, the individual is a non-human mammal. In other aspects, the individual is a dog. In other aspects, the individual is diagnosed with cancer. In other aspects, the individual has cancer. In some aspects, the method further comprises providing the determination of the likelihood of long-term survival to a health care professional who is involved in determining the course of treatment for the individual. In another aspect, the determination of the likelihood of long-term survival is recorded on a fixed medium.

BRIEF DESCRIPTION OF THE DRAWINGS

FIG. 2A depicts the CD3+ index for histomorphometrically characterized tumors. FIG. 2B depicts empirical cumulative distribution of lymphocyte infiltration in tumors from control dogs and dogs that received FasL therapy.

FIG. 4B) and overall survival (OS; FIG. 4C) of dogs treated with FasL that had inflammatory scores of 1 (group 3) versus dogs having inflammatory scores of 2 or 3 (group 2). Data are statistically significant as determined by log rank analysis (p<0.05).

FIG. 5A) and overall survival (OS; FIG. 5B) of dogs treated with FasL having inflammatory scores of 2 or 3 (group 2) versus a contemporary cohort treated with the standard of care (group 1). Data are statistically significant as determined by log rank analysis (p<0.05).

DETAILED DESCRIPTION OF THE INVENTION

Figure 1:
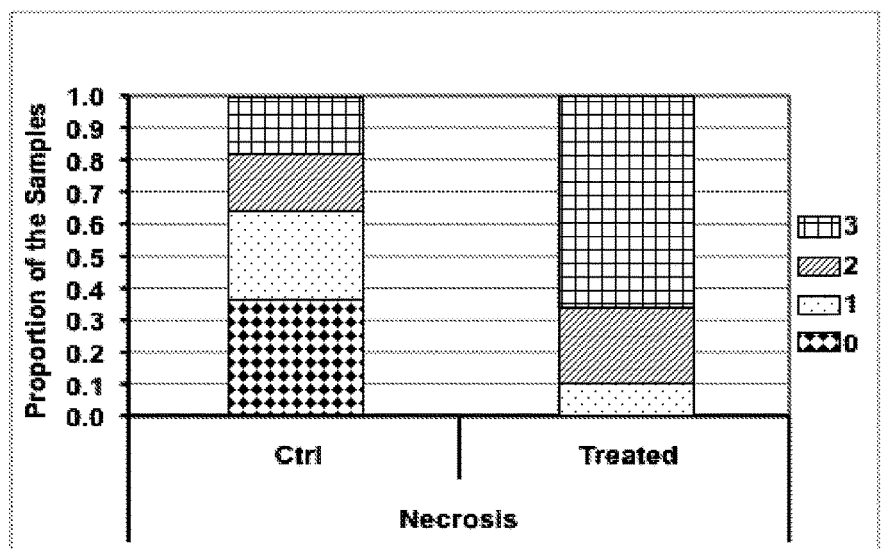
FIG. 1 depicts graphs showing the results of histopathologic evaluation for (A) necrosis, (B) fibrosis, and (C) inflammation in control and treated dogs with spontaneous canine osteosarcoma.
Figure 1:
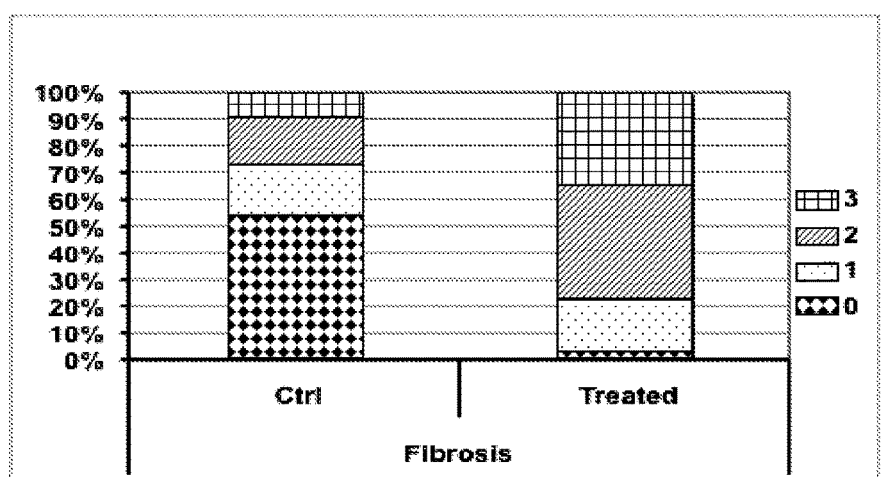
Figure 1:
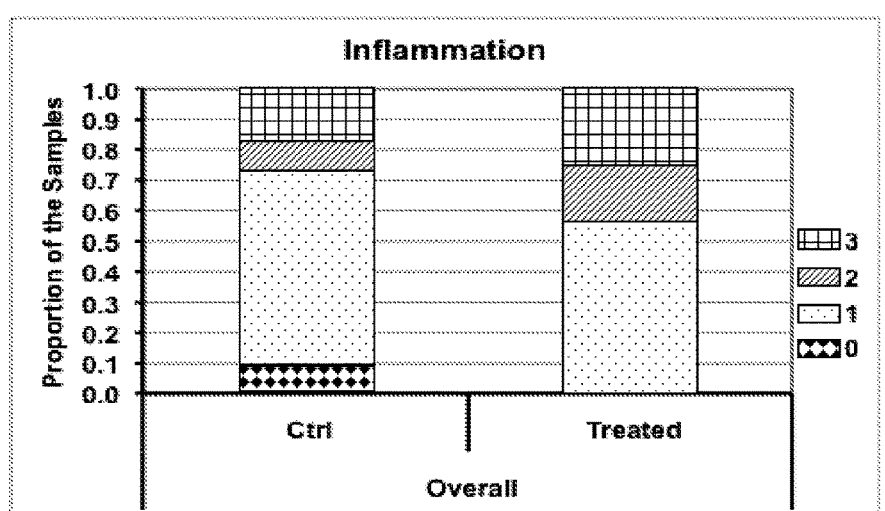

This invention provides, inter alia, methods for determining the likelihood that an individual diagnosed with or suspected of having cancer will receive a beneficial response from an anti-cancer therapy by measuring Fas receptor (Fas) expression levels in a tumor. The invention additionally provides methods of treatment for individuals selected as likely to benefit from anti-cancer therapy based on Fas expression levels. The inventors have observed that reduced Fas expression in or on the surface of tumor cells is associated with localized inflammation in a tumor as well as in surrounding tissue when tumors are treated with FasL. Individuals with tumors exhibiting such localized inflammation experience greater disease free intervals and higher rates of overall survival following treatment with an anti-cancer therapy compared to individuals whose tumors express elevated levels of Fas and whose tumors do not undergo localized inflammation following treatment with FasL. This is useful for selecting individuals or subpopulations of individuals for appropriate treatment and for determining the likelihood of long term survival in individuals with cancerous tumors. This is also useful as part of treating individuals diagnosed with, suspected of having, or having, cancerous tumors through the induction of a localized inflammatory effect within the tumor, leading to subsequent white blood cell infiltration and tumor cell death, including tumor cells which have metastasized away from the location of the primary tumor.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987). Other useful references include Harrison's *Principles of Internal Medicine* (McGraw Hill; J. Isseleacher et al., eds.), *Dubois' Lupus Erythematosus* (5th ed.; D. J. Wallace and B. H. Hahn, eds.; Williams & Wilkins, 1997), *Textbook of Veterinary Internal Medicine: Diseases of the Dog and Cat* (Stephen Ettinger, ed., W.B. Saunders Company; 5th edition (Jan. 15, 2000));

and *Kirk's Current Veterinary Therapy XIV* (Bonagura et al, Saunders; 14 edition (Jul. 10, 2008)).

Definitions

As used herein, the singular form "a", "an", and "the" includes plural references unless indicated otherwise.

An "individual" can be a vertebrate, a mammal, or a human. Mammals include, but are not limited to, farm animals, sport animals (such as, but not limited to, horses), pets, primates, mice and rats. Individuals can also include non-mammalian vertebrates (e.g., lizards, snakes, and birds). Individuals also include companion animals including, but not limited to, dogs and cats. In one aspect, an individual is a human. In another aspect, an individual is a dog.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Methods for Using Fas as a Biomarker

The expression level of Fas receptor (Fas; also known as CD95, Apo-1, and tumor necrosis factor receptor superfamily, member 6 (TNFRSf6)) can be used to determine the likelihood of a beneficial response to an anti-cancer therapy as well as the likelihood of long-term survival in an individual suspected of having or developing cancerous tumors. Additionally provided is a method for using the expression level of Fas to select an individual or subpopulation of individuals who will benefit from anti-cancer therapy. Cancerous tumors that are contemplated include, but are not limited to, sarcoma, osteosarcoma, melanoma, prostate cancer, glioma, urothelial cancers, and head and neck cancers. Any of the methods described herein can be used by health care professionals to aid in a treatment plan or to make treatment decisions by choosing among the most appropriate treatment options for any individual, based on expression levels of Fas in a tumor or a suspected tumor. Similarly, any of the methods described herein can be used for aiding in the diagnosis of an individual or subpopulation of individuals who will benefit from anti-cancer therapy.

Cancers

One aspect of the invention provides for methods of selecting individuals or subpopulations of individuals who have been diagnosed with cancer or are suspected of having cancer. Common cancers contemplated include, but are not limited to, bone cancer, hemangiosarcoma, other sarcomas, mammary cancer, testicular cancer, mast cell cancer, nasosinal cancer, bladder cancer, head and neck cancer, prostate cancer, brain cancer (including gliomas), lung carcinoma, and soft-tissue carcinoma. In addition, other solid tumors known to those having skill in the art are contemplated as well as cancers that metastasize away from sites of primary tumor development. Additional, cancers can include osteosarcoma, a form of bone cancer, as well as melanoma.

Osteosarcoma

Osteosarcoma is a relatively rare form of cancer afflicting a disproportionate percentage of children, with an annual incidence of 900 new individuals per year including 400 who are less than 20 years old. Though rare, it is the $6^{th}$ leading form of cancer in children under the age of 15, totaling about 3% of all childhood cancers. The current standard of care is amputation or limb-salvage orthopedic surgery combined with chemotherapy (high dose methotrexate with leucovorin rescue, intra-arterial cisplatin, adriamycin, ifosfamide, etoposide, and muramyl tri-peptide). Survival rates have improved since the 1960s when the only treatment option was amputation and only 5-20% of diagnosed patients survived more than 2 years. However, despite improvements in chemotherapy, the survival rate for osteosarcoma remains among the lowest for pediatric cancers. The current 5-year survival rate for non-metastatic osteosarcoma patients is greater than 70% while, for patients with metastases, the survival rate is approximately 30%. Progress toward improved treatment options for this young population is slowed by its rare incidence and the resultant challenges in patient accrual for clinical studies.

Melanoma

Skin cancer is the most common of all cancers in the United States. Although melanoma is a relatively uncommon form, accounting for less than 5% of skin cancer cases, it is responsible for 75% of skin cancer deaths. The rate of new cases was relatively stable over the past 8 years, with estimates of 68,720 new cases in 2009 resulting in over 8,650 deaths. According to a World Health Organization report, there are approximately 48,000 melanoma-related deaths worldwide per year. The overall risk of melanoma varies with ethnicity, ranging from 2% for Caucasians to 0.5% for Hispanics and 0.1% in African Americans. Current treatment options include surgical resection and chemotherapy (including single or combination treatments with dacarbazine, carmustine, cisplatin, tamoxifen, vinblastin, temozolomide, and paclitaxel).

Anti-Cancer Therapies

The methods of the invention may be practiced in an adjuvant setting. "Adjuvant setting" refers to a clinical setting in which an individual has had a history of a proliferative disease, particularly cancer, and generally (but not necessarily) has been responsive to therapy, which includes, but is not limited to, surgery, radiotherapy, and chemotherapy. However, because of a history of the proliferative disease (such as cancer), these individuals are considered at risk of developing that disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy. The individual may be a human or may be a non-human mammal. Specifically, the non-human mammal may be a companion animal, such as a dog.

In some aspects, any of the methods described herein include the administration of an effective amount of an anti-cancer therapy to the tumors of individuals having or suspected of having cancerous tumors. As used herein, an "effective amount" or "effective dosage" of an anticancer therapy is an amount sufficient to effect beneficial or desired results. For prophylactic use, beneficial or desired results include results such as eliminating or reducing the risk, lessening the severity, or delaying the onset of carcinogenesis, including biochemical, histological and/or behavioral symptoms of cancer, its complications and intermediate pathological phenotypes presenting during development of cancer. For therapeutic use, beneficial or desired results include clinical results such as decreasing one or more symptoms resulting from cancer, increasing the quality of life of those suffering from cancer, decreasing the dose of other medications required to treat the cancer, enhancing effect of another medication such as via targeting, delaying the progression of the disease, and/or prolonging survival. An effective dosage can be administered in one or more administrations. For purposes of this invention, an effective dosage of an anti-cancer therapy is an amount sufficient to accomplish prophylactic or therapeutic treatment either directly or indirectly. As is understood in the clinical context, an effective dosage of an anti-cancer therapy may or may not be achieved in conjunction with another anti-cancer therapy.

In some aspects, the anti-cancer therapy for any of the methods described herein may be administration of FasL to the tumors of individuals having or suspected of having cancerous tumors. In one aspect, a composition containing an effective amount of FasL is administered to the cancerous tumors of an individual in need thereof. The administration of FasL can be intratumoral administration, which is generally known to one of skill in art. In one aspect, a recombinant vector can be used for delivering FasL to tumors. This can be any vector capable of enabling recombinant production of FasL and/or which can deliver a FasL nucleic acid molecule into a host cell. The vector can be either RNA or DNA, either prokaryotic or eukaryotic, and typically is a virus or a plasmid. The vector may be part of a DNA vaccine or used as part of any other method for delivering a heterologous gene for expression in a host cell that is known to one having skill in the art. Recombinant vectors are capable of replicating when transformed into a suitable host cell. Vectors which may be used, include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art. In one aspect, the anti-cancer therapy for any of the methods described herein includes administration of an effective amount of an adenoviral vector expressing FasL (e.g., Fasaret™) to the tumors of individuals having or suspected of having cancerous tumors.

An adenoviral vector is an example of a vector for use in the present methods for delivering FasL to tumor cells (See, e.g. U.S. Patent Application Publication No. 2004/0224389, which is incorporated by reference herein with respect to disclosure related to delivery of proteins to cells via viral vectors). In some aspects, an adenoviral vector delivers an effective amount of FasL to tumor cells. An adenoviral vector infects a wide range of non-dividing human cells and has been used extensively in live vaccines without adverse side effects. Adenoviral vectors do not integrate into the host genome, and therefore, gene therapy using this system requires periodic administration, although methods have been described which extend the expression time of adenoviral transferred genes, such as administration of antibodies directed against T cell receptors at the site of expression (Sawchuk et al., *Hum. Gene. Ther.* 7:499-506 (1996)). It is noted, however, that for use in the therapeutic methods of the present invention as described herein, it is not necessary that the expression of the FasL by the viral vector be long-term.

In other aspects of any of the methods described herein, an effective amount of FasL is delivered to tumor cells using an AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus. AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" In *Parvoviruses* (J R Kerr, S F Cotmore. M E Bloom, R M Linden, C R Parrish, Eds.) p5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some aspects, any of the methods of treatment described herein can further comprise administering one or more additional anti-cancer therapies to the individual. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anticancer agents that can be used. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

Obtaining Biological Samples from Tumors

Biological samples from tumors can be obtained in various ways. In one aspect, a biological sample is obtained from a tumor which may be a subcutaneously accessible tumor or from any other type of cancerous solid tumor accessible to biopsy or surgical removal. The biological sample may be obtained by any method known in the art including, but not limited to, needle or core biopsy or fine needle aspiration. Additionally, the biological sample may be fixed, paraffin embedded, fresh, or frozen before expression levels of Fas are measured.

Measuring Fas Expression in Tumors

Fas expression in tumors can be used as a biomarker by assessing the expression levels of Fas in a biological sample from an individual or subpopulation of individuals suspected of having or developing cancerous tumors. Fas expression in tumors can also be used as a biomarker by assessing the expression levels of Fas in a biological sample from an individual or subpopulation of individuals with cancerous tumors. Fas can be expressed either within a cell or on the surface of a cell as a component of the plasma membrane. Fas expression encompasses the existence of the full and intact Fas DNA sequence (including, e.g., promoter elements, enhancer sequences, introns, and exons), the conversion of the Fas DNA gene sequence into transcribed mRNA (including, e.g., the initial unspliced mRNA transcript or the mature processed mRNA), or the translated Fas protein product (including, e.g. any posttranslational modifications such as, but not limited to, ubiquitination, sumoylation, acetylation, methylation, glycosylation, and/or hydroxylation).

The assessment of Fas expression can be at the levels of protein, mRNA, or DNA. Assessment of mRNA expression levels of gene transcripts is routine and well known in the art. For example, one flexible and sensitive quantitative method for assessing mRNA expression levels in a biological sample is by quantitative RT-PCR (qRT-PCR) or by any other comparable quantitative PCR-based method. Additional methods for assessing Fas mRNA expression include, but are not limited to, Northern blotting, microarrays, in situ hybridization, and serial analysis of gene expression (SAGE).

Similarly, assessment of protein expression levels is routine in the art. For example, one method of measuring protein levels is via Western blotting or immunohistochemistry using commercially-available antibodies to Fas. However, without being bound to theory, there is an inverse correlation between the expression level of Fas protein and the likelihood of a beneficial response to an anti-cancer therapy, where the anticancer therapy includes treatment with a composition comprising FasL. In some aspects, the anticancer therapy includes treatment with an adenoviral vector expressing FasL (e.g., Fasaret™). Also, without being bound to theory, there is an inverse correlation between the expression level of Fas protein and the likelihood of long-term survival in an individual suspected of having or developing cancerous tumors. Consequently, the sensitivity of the protein assay is particularly important. Therefore, RIA, ELISA, flow cytometry, or any other more sensitive quantitative method of measuring Fas protein expression can be used instead of less quantitative methods.

A characteristic of many forms of cancer is an increase in chromosomal rearrangements and translocations as well as gene mutations within neoplastic cells. Previous research has indicated that chromosome 26, the location of Fas in dogs, is particularly unstable in many different cancers and prone to chromosomal rearrangement and deletion (Thomas et al., *Cytogenet. Genome Res.* 102(1-4):254-60 (2003)). Assessment of DNA to examine whether a particular gene has been mutated or deleted in a population or subpopulation of cells is routine in the art. For example, one method for detecting whether the Fas gene sequence in an individual's genomic DNA has been mutated during the course of carcinogenesis is Southern Blotting, which combines transfer of electrophoresis-separated DNA fragments to a filter membrane and subsequent fragment detection by probe hybridization. Another method is PCR of one or more segments of the Fas gene followed by either restriction digestion or DNA sequencing by any method known in the art.

Fas protein or mRNA expression levels can be measured from biological samples obtained from the tumors of individuals suspected of having or developing cancerous tumors and can be normalized to the expression levels of one or more reference genes expressed in the sample. Normalization, with regard to protein or mRNA expression levels, can be done by measuring the level of the mRNA transcript or protein product of interest relative to the mean levels of transcripts/products of one or more reference genes, wherein the reference genes are either selected based on their minimal variation across individuals, tissues, or treatments or are the totality of tested genes. In the latter case, commonly referred to as "global normalization," the total number of tested genes must be relatively large, preferably greater than 50. Specifically, the term "normalized" with respect to a particular mRNA transcript can refer to the transcript expression level relative to the mean of transcript levels of one or more reference, or "housekeeping," genes. Suitable housekeeping genes are ideally expressed at a constant level among different tissues and are unaffected by treatment or disease state. Messenger RNAs that can be used as housekeeping genes include, but are not limited to, Ubiquitin (Ub), glyceraldehyde-3-phosphate-dehydrogenase (GAPDH), and β-actin.

In some aspects, quantitative RT-PCT (qRT-PCR) is employed to assess normalized Fas mRNA expression levels. When using qRT-PCR, a housekeeping gene, for example GAPDH, is used to normalize expression levels of Fas in a biological sample. Quantitative RT-PCR measures mRNA expression in CT (threshold cycle) units (Held et al., Genome Research 6:986-994 (1996)). The averaged sum of CTs for one or more housekeeping mRNAs is arbitrarily set (e.g. to one), and each measured mRNA CT for the particular transcript of interest is given a value relative to this fixed reference. For example, if, for a particular individual's biological sample, the average of the CTs for the housekeeping gene (e.g., GAPDH) is found to be 31 and the CT for Fas mRNA is found to be 35, then the reported normalized value for Fas would be −4 (i.e. 31-35). The normalized qRT-PCR values of Fas expression from all biological samples tested are then numerically ranked according to normalized value. The median ranked value is selected as a "calibration value" and this particular individual's biological sample is assigned a "calibration score" of "1." Normalized qRT-PCR values from all other samples tested are then calibrated to that of this median value to obtain calibration scores for each sample tested by dividing the median normalized qRT-PCR calibration value by the normalized qRT-PCR value of each individual sample.

In other aspects, immunohistochemistry (IHC) is employed to assess Fas protein levels in tissue samples (such as a tissue sample from a cancerous tumor). Tissue sections can be stained using an anti-Fas antibody according to methods which are well known in the art. The tissue sections can be prepared any number of ways according to commonly known techniques. For example, the tissue sections may be cryopreserved or the sections may be fixed (such as with a fixative agent such as formaldehyde, paraformaldehyde, or gluteraldehyde) and embedded (such as embedded in paraffin wax or polyester wax). When using IHC, a semiquantitative score can be used to define the amount of Fas protein in a tissue sample wherein the score ranges from 0 to 4+. Using this method, a score of 0 shows that the amount of Fas protein staining does not differ from that of the background in the section whereas a score of 4+ indicates that Fas staining is equivalent to leukocytes (e.g., neutrophils) in the section. Since neutrophils can be found in virtually any tissue section (i.e. within or outside of blood vessels, within the tumor, or in adjacent normal tissue), they can be used as an internal positive control for the expression of Fas in tissue sections. In some aspects, the lowest score in a range of staining intensities can be determinative as to whether the tissue section contains cells expressing "low" or "high" levels of Fas. For example, if the range is 0-2, then the determinant is 0 and the level of Fas expression in the tissue section is low. If the range is 2-4, the determinant is 2 and the level of Fas expression in the tissue section is high. In other aspects, when the lowest determinant score in a tissue section with variable staining intensities is 0, the cells have low Fas protein expression levels. In another aspect, when the lowest determinant score in a tissue section with variable staining is >0, the cells have high Fas protein expression levels.

In some aspects, the score can be obtained using an automated device for assessing optical density of a stained tissue section. For example, the amount of Fas protein in a tissue section can be quantitated from an average optical density (OD) of IHC-labeled Fas protein per pixel in a defined cellular area. The amount of Fas protein in normal cells and tumor cells can be quantitated from an average OD determined for the tumor cells and the normal cells on a per cell basis in the tissue section. The average OD on a per cell basis is obtained by dividing the average OD for the cells in the tissue section by the number of nuclei in the tissue section. In some aspects, the average optical density can be determined by using an automated image analysis system (for example, but not limited to, a system such as the Aperio™).

In one aspect, when an automated device for assessing optical density of an IHC-stained tissue section is used, the expression of Fas protein in tumor cells can be quantified by reference to the expression of non-tumor cells in the tissue section that are known to express Fas. For example, Fas-expressing neutrophils can be found in virtually any tissue section (within or outside blood vessels), within a tumor, or in adjacent normal tissue. The optical density (measured, e.g., in pixels/mm2) of immunohistochemically-labeled Fas protein in neutrophils within a tissue section can be assigned a normalized score of 100 while cells that are known to lack Fas expression and show no differential staining from the background can be assigned a score of 0. The averaged optical density scores of IHC-stained tumor cells can then be normalized relative to the average optical density score for Fas expression in neutrophils within a tissue section. In some aspects, when an automated device for assessing optical density of an IHC-stained tissue section is used, the term "decreased Fas expression" or "low Fas expression" can refer to normalized scores of Fas expression in tumor cells of at most about 50, such as about 45, 40, 35, 30, 25, 20, 15, 10, 5, inclusive, as well as any numerical value in between these numbers. In other aspects, decreased or low Fas expression can refer to normalized scores of Fas expression in tumor cells of at least about 1, such as about 5, 10, 15, 20, 25, 30, 35, 40, 45, or 49, inclusive, as well as any numerical value in between these numbers. In still other aspects, when an automated device for assessing optical density of an IHC-stained tissue section is used, the term "increased Fas expression" or "high Fas expression" can refer to normalized scores of Fas expression in tumor cells of at most about 100, such as about 95, 90, 85, 80, 75, 70, 65, 60, 55, or 51, inclusive, as well as any numerical value in between these numbers. In another aspect, increased or high Fas expression can refer to normalized scores of Fas expression in tumor cells of at least about 51, such as about 55, 60, 65, 70, 75, 80, 85, 90, 95, or 100, inclusive, as well as any numerical value in between these numbers.

Accordingly, in one aspect, low or decreased Fas expression can refer to a quantitative amount, as described herein, or a qualitative amount by reference to a normalization standard, as described herein.

Methods for Assessing the Likelihood of a Beneficial Response to an Anti-Cancer Therapy Method of assessing the likelihood of a beneficial response to an anti-cancer therapy in an individual suspected of having or developing cancerous tumors can be accomplished using the methodologies described herein. A decreased Fas expression level in a biological sample from the individual is inversely correlated with the likelihood of a beneficial response to an anti-cancer therapy, where the anticancer therapy includes treatment with a composition comprising FasL. In some aspects, the anti-cancer therapy includes treatment with an adenoviral vector expressing FasL (e.g., Fasaret™). Likelihood of a beneficial response can mean that the likelihood that cancer-attributable death, progression, recurrence, metastatic spread, and/or drug resistance of a neoplastic disease is decreased relative to an individual having high expression levels of Fas in a tumor. Beneficial response can refer to an individual responding favorably to one or more drugs, a tumor shrinking or otherwise decreasing in size, a decrease in the amount of tumor metastasis away from the primary tumor site, and also the extent of that favorable response, or that an individual will survive, following surgery to remove a primary tumor and/or chemotherapy for a certain period of time without cancer recurrence. Beneficial response may also refer to an individual surviving longer with stable disease. In other words, tumors may remain and be detectable, but will not cause significant morbidity or death for the individual.

In some aspects, the individual suspected of having or developing cancerous tumors may be a human or may be a non-human mammal. Specifically, the non-human mammal may be a companion animal, such as a dog. The individual may further be diagnosed with cancer.

The biological sample may be obtained and normalized expression levels of Fas determined by any of the methods described herein. In one aspect, a normalized expression level of Fas is determined by qRT-PCR. When qRT-PCR is used, the term "decreased Fas expression" refers to calibration scores of less than 1, such as 0.001 to 0.009, 0.01 to 0.09, or 0.1 to 0.999 inclusive, as well as any numerical value in between these ranges. In another aspect, when qRT-PCR is used, decreased Fas expression refers to calibration scores of at least about 0.0001, 0.001, 0.01, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 0.96, 0.97, 0.98, or 0.99, inclusive, as well as any numerical value in between these numbers. In some aspects, when qRT-PCR is used, decreased Fas expression refers to calibration scores of at most about 0.99, 0.95, 0.9, 0.8, 0.7, 0.6, 0.5, 0.4, 0.3, 0.2, 0.1, 0.01, 0.001, 0.0001, or 0.00001, inclusive, as well as any numerical value in between these numbers. In other aspects, a quantitative expression level of Fas is determined by IHC. When IHC is used, the term "decreased Fas expression" refers to tissue samples with a score of 0 to 2, where at least a subset of tumor cells exhibit no expression of Fas protein (score=0) and where the maximal score for the tissue section is <2.

In another aspect, the methods of assessing the likelihood of a beneficial response to an anti-cancer therapy in an individual suspected of having or developing cancerous tumors can further include providing the assessment to a healthcare professional. A healthcare professional can include, without limitation, doctors, nurses, physician assistants, lab technicians, research scientists, clerical workers employed by the same, or any person involved in determining, diagnosing, aiding in the diagnosis or influencing the course of treatment for the individual.

Fixed or Data-Storage Media

The assessment of the likelihood of a beneficial response to an anti-cancer therapy in an individual suspected of having or developing cancerous tumors may be provided to the healthcare professional by being recorded on a fixed or data storage medium and/or being accessible via a system for reading the storage medium. For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data may also be contemplated for communication of the assessment of the likelihood of a beneficial response to an anti-cancer therapy in an individual suspected of having or developing cancerous tumors to a healthcare professional.

Methods for Identifying or Selecting an Individual who can Benefit from Anti-Cancer Therapy Using the methodologies described herein, one of skill in the art can identify and/or select individuals or subpopulation of individuals who can benefit from anti-cancer therapy. In some aspects, there is provided a method of selecting an individual who can benefit from anti-cancer therapy. The anti-cancer therapy can include treatment with a composition containing FasL (such as, but not limited to, an adenoviral vector expressing FasL (e.g., Fasaret™)). A low Fas expression level in a biological sample from an individual indicates that the individual can benefit from anti-cancer therapy. The biological sample may be obtained and normalized expression levels of Fas determined by any of the methods described herein. In some aspects, a normalized expression level of Fas is determined by qRT-PCR. In one aspect, when qRT-PCR is used, the term "low Fas expression" refers to calibration scores of less than 1, such as 0.001 to 0.009, 0.01 to 0.09, or 0.1 to 0.999 inclusive, as well as any numerical value in between these ranges. In another aspect, when qRT-PCR is used, decreased Fas expression refers to calibration scores of at least about 0.0001, 0.001, 0.01, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 0.96, 0.97, 0.98, or 0.99, inclusive, as well as any numerical value in between these numbers. In some aspects, when qRT-PCR is used, decreased Fas expression refers to calibration scores of at most about 0.99, 0.95, 0.9, 0.8, 0.7, 0.6, 0.5, 0.4, 0.3, 0.2, 0.1, 0.01, 0.001, 0.0001, or 0.00001, inclusive, as well as any numerical value in between these numbers. In other aspects, a quantitative expression level of Fas is determined by IHC. When IHC is used, the term "decreased Fas expression" refers to tissue samples with a score of 0 to 2, where at least a subset of tumor cells exhibit no expression of Fas protein (score=0) and where the maximal score for the tissue section is <2.

In some aspects, the individual who is selected may be a human or may be a non-human mammal. Specifically, the non-human mammal may be a companion animal, such as a dog. The individual may further be diagnosed with cancer.

In one aspect, the method of selecting an individual who can benefit from anti-cancer therapy further comprises providing the selection of the individual who will benefit from anti-cancer therapy to a healthcare professional. A healthcare professional can include, without limitation, doctors, nurses, physician assistants, lab technicians, research scientists, clerical workers employed by the same, or any person involved in determining, diagnosing, aiding in the diagnosis or influencing the course of treatment for the individual. The selection may be provided to the healthcare professional by being recorded on a fixed or data storage medium and/or being accessible via a system for reading the storage medium. The system for reading the storage medium can utilize any of the fixed or data-storage media described herein or any other system known to one of skill in the art.

Methods for Determining Likelihood of Long Term Survival

Determination of likelihood of long term survival can be calculated by using the methodologies described herein. The term "long-term survival" is used herein to refer to survival for at least 1 year, 5 years, 8 years, or 10 years following diagnosis of cancer. In some aspects, there is provided a method of determining the likelihood of long term survival in an individual suspected of having or developing cancerous tumors. Decreased Fas expression level in a biological sample from the individual is inversely correlated with the likelihood of long term survival in an individual with cancerous tumors. The biological sample may be obtained and normalized expression levels of Fas determined by any of the methods described herein. In some aspects, a normalized expression level of Fas is determined by qRT-PCR. When qRT-PCR is used, the term "decreased Fas expression" refers to calibration scores of less than 1, such as 0.001 to 0.009, 0.01 to 0.09, or 0.1 to 0.999 inclusive, as well as any numerical value in between these ranges. In another aspect, when qRT-PCR is used, decreased Fas expression refers to calibration scores of at least about 0.0001, 0.001, 0.01, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 0.96, 0.97, 0.98, or 0.99, inclusive, as well as any numerical value in between these numbers. In some aspects, when qRT-PCR is used, decreased Fas expression refers to calibration scores of at most about 0.99, 0.95, 0.9, 0.8, 0.7, 0.6, 0.5, 0.4, 0.3, 0.2, 0.1, 0.01, 0.001, 0.0001, or 0.00001, inclusive, as well as any numerical value in between these numbers. In other aspects, a quantitative expression level of Fas is determined by IHC. When IHC is used, the term "decreased Fas expression" refers to tissue samples with a score of 0 to 2, where at least a subset of tumor cells exhibit no expression of Fas protein (score=0) and where the maximal score for the tissue section is <2.

In some aspects, the individual suspected of having or developing cancerous tumors may be a human or may be a non-human mammal. Specifically, the non-human mammal may be a companion animal, such as a dog. The individual may further be diagnosed with cancer.

In one aspect, the method of determining the likelihood of long term survival in an individual suspected of having or developing cancerous tumors further comprises providing the determination to a healthcare professional. A healthcare professional can include, without limitation, doctors, nurses, physician assistants, lab technicians, research scientists, clerical workers employed by the same, or any person involved in determining, diagnosing, aiding in the diagnosis or influencing the course of treatment for the individual. The determination may be provided to the healthcare professional by being recorded on a fixed or data storage medium and/or being accessible via a system for reading the storage medium. The system for reading the storage medium can utilize any of the fixed or data-storage media described herein or any other system known to one of skill in the art.

Methods of Treatment for Selected Individuals or Subpopulations of Individuals

The invention further provides methods of treatment for individuals or subpopulations of individuals selected as likely to benefit from anti-cancer therapy where the selection is based on low or decreased levels of Fas expression in tumors. The determination of the Fas expression in tumors and/or on tumor cells can be achieved as described in any of the methods herein. Additionally, there is provided a method for inducing a localized inflammatory effect in an individual or subpopulations of individuals suspected of having or developing solid tumors based on the level of Fas expression in the tumor cells from the individual.

Methods of Treatment for Selected Individuals with Low Levels of Fas Expression in Tumors Individuals with tumors or suspected of having tumors can be selected first and then treated with FasL therapy. The individual or subpopulations of individuals are selected for treatment based on low Fas expression in the tumor cells from the individual, which can be determined by any of the methods described herein. The individual can be treated by administration of a composition comprising FasL to the tumor. In some cases, the administration is intratumoral. The composition may comprise the FasL gene in an adenoviral vector. In some aspects, the composition is an adenoviral vector expressing FasL (e.g., Fasaret™). In another aspect, an individual is administered a composition comprising FasL more than one time (e.g., for a non-resectable tumor recurrence), wherein the same interval of time between administrations is used after each administration.

Administration of a composition comprising FasL to an individual selected for treatment based on low Fas expression in the tumor cells from the individual promotes localized inflammation in the tumor as well as in the tissue surrounding the tumor. This localized inflammation response can be characterized by increases in tumor cell necrosis, apoptosis, fibrosis, and/or infiltration of white blood cells within the tumor. Initially following administration of the composition comprising FasL, infiltrating white blood cells can be neutrophils. However, if inflammation persists over time following administration of the composition comprising FasL, for example, for 4, 5, 6, 7, 8, 9, 10, 11, 12, 13, 14, 15-25 or greater than 25 days, inclusive, as well as any numerical value in between these ranges, the infiltrating white blood cells are lymphocytes, including, but not limited to, CD3+ lymphocytes. The infiltrating white blood cells can also include monocytes and/or macrophages.

The individual suspected of having or developing cancerous tumors may be a human or may be a non-human mammal. Specifically, the non-human mammal may be a companion animal, such as a dog. The individual may further be diagnosed with cancer, including, but not limited to, osteosarcoma or melanoma. In some aspects, the cancer is a metastatic cancer. The individual's cancer can be induced via exposure to carcinogens or some other toxin found either in the environment or research laboratory setting. In other aspects, the cancer can be naturally occurring. In some aspects, the method further comprises administering one or more additional anti-cancer therapies to the individual, including any of the anti-cancer therapies described herein.

In some aspects, provided herein are compositions comprising an effective amount of FasL for use in treating cancer in an individual, wherein the individual has low Fas expression in the cells of a cancerous tumor, as determined by any of the methods described herein.

Methods of Treatment for Selected Individuals with High Levels of Fas Expression in Tumors In some aspects, there is provided a method of treating an individual suspected of having or developing cancerous tumors. The individual is selected for treatment based on high Fas expression in the tumor cells from the individual, which can be determined by any of the methods described herein. For example, when qRT-PCR is used to assess expression levels of Fas in a tumor, the term "high Fas expression" can refer to calibration scores of greater than or equal to 1, such as 1, 1.1, 1.2, 1.3, 1.4, 1.5, 1.6, 1.7, 1.8, 1.9, 2, 3, 4, 5, 10, 100, 1000, 10,000, or greater than 10,000, inclusive, as well as any numerical value in between these numbers. In other aspects, when qRT-PCR is used to assess expression levels of Fas in a tumor, high Fas expression can refer to calibration scores less than or equal to about 10,000, 1000, 100, 100, 10, 5, 4, 3, 2, 1.9, 1.8, 1.7, 1.6, 1.5, 1.4, 1.3, 1.2, or 1, inclusive, as well as any numerical value in between these numbers. "High Fas expression" can refer to calibration scores of about 1-10,000 inclusive (such as from 1-2, 1-5, 1-10, 1-50, 1-100, 1-500, 1-750, 1-1000, 1-5000, or 1-7,500), as well as any numerical value in between these ranges. In other aspects, when IHC is used to assess expression levels of Fas in a tumor, the term "high Fas expression" refers to tissue samples with a score of 2+ to 4+, where the tissue section exhibits consistent expression of Fas in every cell (4+) and/or where the minimum score for the tissue section is 2.

If an individual is selected for treatment based on high Fas expression in tumor cells, the individual is first administered a composition which blocks (such as completely blocks) the interaction between FasL and Fas in the tumor and which does not result in Fas-mediated programmed cell death. In some aspects, the composition which blocks the interaction between FasL and Fas in the tumor can partially block the interaction between FasL and Fas by about any of 20%, 30%, 40%, 50%, 60%, 70%, 80%, 90%, 95%, or, 99%, inclusive, including any percentages in between these values, compared to the level of interaction of FasL and Fas in the absence of the composition. In some aspects the composition which blocks the interaction between FasL and Fas in the tumor results in a minimal amount of Fas-mediated programmed cell death, such as no more than about 1%, 2%, 3%, 4%, 5%, 6%, 7%, 8%, 9%, or 10% of the Fas-mediated program cell death resulting from the interaction between FasL and Fas. Techniques for determining whether a composition can block the interaction between two proteins (such as Fas and FasL) are numerous and well known in the art and include, for example, quantitative ELISA, radioimmunoassay, pull down assays, immunoprecipitation, and surface plasmon resonance. Techniques for determining whether a composition results in Fas-mediated programmed cell death are numerous and well known in the art and include, for example, Western blots (using antibodies specific for caspases activated by the interaction between Fas and FasL, such as caspase 8), TUNEL assays, or annexin V assays.

The composition which blocks the interaction between FasL and Fas can be an antibody to Fas which does not initiate apoptosis. Additionally, the composition which blocks the interaction between FasL and Fas can be an antisense oligonucleotide or an siRNA directed to Fas which results in decreased cellular Fas expression. Antisense oligonucleotides and siRNAs for reducing cellular Fas expression levels are known in the art (See, e.g., Mao, et al., *Int Immunopharmacol.*, 7(13):1714-22 (2007); Tsujii et al., *J. Biochem.* 148(2):157-70 (2010)).

In some aspects, the composition which blocks the interaction between FasL and Fas in the tumor and which does not result in Fas-mediated programmed cell death is a non-antibody binding polypeptide. Binding polypeptides are polypeptides that bind, preferably specifically, to Fas and which do not initiate programmed cell death. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to Fas. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl.*

*Acad. Sci. U.S.A.,* 82:178-182 (1985); Geysen et al., in Synthetic Peptides as Antigens, 130-149 (1986); Geysen et al., *J. Immunol. Meth.,* 102:259-274 (1987); Schoofs et al., *J. Immunol.,* 140:611-616 (1988), Cwirla, S. E. et al., (1990) *Proc. Natl. Acad. Sci. USA,* 87:6378; Lowman, H. B. et al., (1991) *Biochemistry,* 30:10832; Clackson, T. et al., (1991) *Nature,* 352: 624; Marks, J. D. et al., (1991), *J. Mol. Biol.,* 222:581; Kang, A. S. et al., (1991) *Proc. Natl. Acad. Sci. USA,* 88:8363, and Smith, G. P. (1991) *Current Opin. Biotechnol.,* 2:668).

In some aspects, the composition which blocks the interaction between FasL and Fas in the tumor and which does not result in Fas-mediated programmed cell death is an antibody. Antibodies are proteins that bind, preferably specifically, to Fas. Variants of antibodies can be made based on information known in the art, without substantially affecting the activity of antibody. For example, antibody variants can have at least one amino acid residue in the antibody molecule replaced by a different residue. Fragments of antibodies may also be used (such as, but not limited to, Fv, Fab, Fab', or F(ab)$_2$ fragments), as well as genetically-engineered antibodies or antigen binding fragments thereof, including single chain antibodies, humanized antibodies, antibodies that can bind to more than one epitope (e.g., bi-specific antibodies), or antibodies that can bind to one or more different antigens (e.g., bi- or multi-specific antibodies), may also be employed. For antibodies, the sites of greatest interest for substitutional mutagenesis generally include the hypervariable regions, but framework region (FR) alterations are also contemplated. For antibodies, one type of substitutional variant involves substituting one or more hypervariable region residues of a parent antibody (e.g. a humanized or human antibody). Generally, the resulting variant(s) selected for further development will have improved biological properties (e.g., affinity) relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In some aspects, the composition which blocks the interaction between FasL and Fas in the tumor and which does not result in Fas-mediated programmed cell death is a small molecule chemical compound. Small molecules can be molecules other than binding polypeptides or antibodies as defined herein that bind to Fas and which do not initiate programmed cell death. Small molecules may be identified and chemically synthesized using known methodology (see, e.g., International Patent Application Publication Nos. WO00/00823 and WO00/39585). Small molecules are usually less than about 2000 Daltons in size or alternatively less than about 1500, 750, 500, 250 or 200 Daltons in size, wherein such small molecules that are capable of binding, preferably specifically, to a Fas polypeptide as described herein may be identified without undue experimentation using well known techniques. In this regard, it is noted that techniques for screening small molecule libraries for molecules that are capable of binding to a polypeptide target are well known in the art (see, e.g., PCT Publication Nos. WO00/00823 and WO00/39585). Small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

The small molecule chemical compound may be a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as a Fas protein) or mediating a biological activity of interest (such as, but not limited to, inhibition of cellular proliferation). Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

Following administration of a compound which blocks the interaction between FasL and Fas, a composition comprising FasL is administered to the tumor (i.e., sequentially). In some aspects, the compound which blocks the interaction between FasL and Fas and a composition comprising FasL is administered to the tumor simultaneously. The composition comprising FasL may be FasL gene in an adenoviral vector. In some aspects, the composition comprising FasL is an adenoviral vector expressing FasL (e.g., Fasaret™).

Administration of a composition which blocks the interaction between FasL and Fas to a tumor and which does not result in Fas-mediated programmed cell death followed by administration of a composition comprising FasL promotes localized inflammation in the tumor as well as in the tissue surrounding the tumor. This localized inflammation response is characterized by increases in tumoral necrosis, apoptosis, and fibrosis as well as infiltration of white blood cells within the tumor. Initially following administration of the composition comprising FasL, infiltrating white blood cells are neutrophils. However, if inflammation persists over time following administration of the composition comprising FasL, for example, for 4, 5, 6, 7, 8, 9, 10, 11, 12, 13, 14, 15-25 or greater than 25 days, inclusive, as well as any numerical value in between these ranges, the infiltrating white blood cells are lymphocytes, including, but not limited to, CD3+ lymphocytes. The infiltrating white blood cells can also include monocytes and/or macrophages.

The individual suspected of having or developing cancerous tumors may be a human or may be a non-human mammal. Specifically, the non-human mammal may be a companion animal, such as a dog. The individual may further be diagnosed with cancer, including, but not limited to, osteosarcoma or melanoma. In some aspects, the cancer is a metastatic cancer. The individual's cancer can be induced via exposure to carcinogens or some other toxin found either in the environment or research laboratory setting or the cancer can be naturally occurring. In some aspects, the method further comprises administering one or more additional anti-cancer therapies to the individual.

In some aspects, provided herein is a composition which blocks the interaction between FasL and Fas (such as any of the compositions described herein) and an effective amount of a composition comprising FasL for use in treating cancer in an individual, wherein the individual has high Fas expression in the cells of a cancerous tumor, as determined by any of the methods described herein, and wherein the composition which blocks the interaction between FasL and Fas and the composition comprising FasL are administered to the individual simultaneously or sequentially.

Methods for Inducing a Localized Inflammatory Effect

One of skill in the art can use the teachings described herein to induce a localized inflammatory response in individuals in need thereof. In some aspects, induction of a localized inflammatory effect in an individual suspected of having or developing cancerous tumors is achieved using the methodologies provided herein. The individual is selected for treatment based on low Fas expression in the tumor cells from the individual, which can be determined by any of the methods described herein. The individual is treated by administration of a composition comprising FasL to the tumor. The composition may comprise the FasL gene in an adenoviral vector. In some aspects, the composition is an adenoviral vector expressing FasL (e.g., Fasaret™).

The localized inflammatory effect is characterized by increases in tumoral necrosis, apoptosis, and fibrosis as well as infiltration of white blood cells within the tumor. Initially following administration of a composition comprising FasL, infiltrating white blood cells are neutrophils. However, if inflammation persists over time following administration of a composition comprising FasL, for example, for 4, 5, 6, 7, 8, 9, 10, 11, 12, 13, 14, 15-25 or greater than 25 days, inclusive, as well as any numerical value in between these ranges the infiltrating white blood cells are lymphocytes, including, but not limited to, CD3+ lymphocytes. The infiltrating white blood cells can also include monocytes and/or macrophages.

The individual suspected of having or developing cancerous tumors may be a human or may be a non-human mammal. Specifically, the non-human mammal may be a companion animal, such as a dog. The individual may further be diagnosed with cancer, including, but not limited to, osteosarcoma or melanoma. In some aspects, the cancer is a metastatic cancer. The individual's cancer can be induced via exposure to carcinogens or some other toxin found either in the environment or research laboratory setting or the cancer can be naturally occurring. In some aspects, the method further comprises administering one or more additional anti-cancer therapies to the individual.

In some aspects, provided herein are compositions comprising an effective amount of FasL for use in inducing a localized inflammatory response in individual, wherein the individual has low Fas expression in the cells of a cancerous tumor, as determined by any of the methods described herein.

Veterinary Applications

Also contemplated are uses of any of the methods described herein in a veterinary setting. A veterinary setting can include, without limitation, any medical practice that deals with the application of medical, surgical, public health, dental, diagnostic, and therapeutic principles to non-human animals, including wildlife, domesticated animals, livestock, working animals, zoo animals, and companion animals. Animals commonly encountered in a veterinary setting include, but are not limited to, farm animals (e.g. cows, sheep, llamas, deer, bison, goats, pigs), sport animals (e.g. horses, mules, donkeys, greyhounds, hunting dogs), pets, companion animals (e.g., dogs, cats), primates (e.g. tarsiers, monkeys, apes, lemurs, gibbons), rodents (e.g. mice, rats), and rabbits.

Companion animals such as dogs develop various types of spontaneously occurring cancers as well as cancers that develop due to exposure to carcinogens or some other environmental toxin. Common cancers include, but are not limited to, bone cancer, hemangiosarcoma, other sarcomas, mammary cancer, testicular cancer, mast cell cancer, nasosinal cancer, bladder cancer, head and neck cancer, prostate cancer, brain cancers (including gliomas), lung carcinoma, and soft-tissue carcinoma. Some breeds develop certain cancers more often than other breeds. For example, hemangiosarcomas, an aggressive cancer that arises from the blood vessels, are seen more in German Shepherds, Golden Retrievers, Boxers, and English Setters than other breeds. In addition, other solid tumors known to those having skill in the art are contemplated as well.

In contrast to human incidence, osteosarcoma is a relatively common cancer in larger breeds of dogs (>60 pounds), particularly in Great Dane, Wolfhound, and Rottweiler. The incidence of osteosarcoma is 3-4% of all canine cancers, afflicting up to 10,000 dogs per year in North America. Human and canine osteosarcoma share common features of anatomical distribution and metastasis. In both species, >75% of cases occur in long bones (distal radius>proximal humerus; distal femur>tibia), predominantly in males (2:1). The high metastatic rate in dogs (90%) is comparable to that in humans (80%), and sites of metastasis have a similar hierarchy of lung>bone>soft tissue. Furthermore, primary osteosarcoma and metastases are histologically indistinguishable between human and canine patients. Like humans, dogs also respond to chemotherapy-treatment with cisplatin, doxorubicin, or carboplatin following amputation produces a mean survival time of 9-11 months, a significant improvement over the median survival of 3-4 months following amputation alone. Additionally, analysis of gene expression in cells derived from canine and human osteosacroma tumors has been reported to have a remarkable similarity with respect to molecular signatures and associated biological behaviors (see, e.g., Scott et al., 2011, *Bone*, 49:356-367, the disclosure of which is incorporated by reference herein in its entirety). Thus, the use of dogs as a model for cancer treatment in humans is accepted by the scientific community.

Melanoma is the fourth most common cancer in dogs, frequently occurring in the oral cavity but also originating in the digits, skin, and eye. Oral melanoma is reportedly most commonly observed in Dachshunds, Golden Retrievers, Poodles, and Scottish Terriers. As with advanced melanomas in humans, melanomas in dogs are generally resistant to chemotherapy and radiation, and aggressive metastasis is the primary cause of treatment failure and death.

EXAMPLES

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1: FasL Therapy Promotes Inflammation, Necrosis, and Fibrosis in Spontaneous Canine Osteosarcoma In this study, dogs with appendicular osteosarcoma (OS) received doses of FasL administered in an adenoviral vector to tumors to examine the effects of FasL therapy on solid tumors. In addition, histopathological evaluation of tumors 10 days after therapy was administered was conducted to determine the extent of inflammation, necrosis, and fibrosis, if any, caused by the therapy.

Materials and Methods

Patient Selection:

Canine patients with spontaneously occurring OS who presented for treatment to the participating institutions (Animal Cancer Center at Colorado State University (CSU-ACC) or the University of Minnesota, College of Veterinary Medicine (U Minn)) were screened for eligibility. Eligibility criteria included dogs with a diagnosis of stage I (low grade with no detectable metastases based on physical exam and radiographic findings) or stage II (present outside the periosteum with no detectable metastases based on physical exam and radiographic findings), substage a (intracompartmental) or substage b (extracompartmental) appendicular osteosarcoma that were otherwise in good enough health to tolerate diagnostic and treatment procedures (including biopsy and amputation) were eligible to participate in this study. Additional eligibility criteria included patient age between 2-12 years; either sex and any breed; body weight >20 kg; performance status and adequate health to tolerate biopsy, gene therapy, and 10-day delay for standard-of-care treatment (amputation and adjuvant chemotherapy), and no other preexisting acute or chronic disease present that would preclude a one-year lifespan. Diagnostic tests to screen for eligibility included complete clinical history, physical exam, CBC, biochemical profile, urinalysis, chest radiographs for metastasis evaluation, and in some cases whole body nuclear bone scan. Patients were required to have adequate laboratory and clinical indices to safely undergo therapy, specifically transaminases not exceeding 3× normal, total bilirubin not exceeding 1.5× normal, creatinine not exceeding 2× normal, at least 2500 neutrophils/ul, 75,000 platelets/ul, and a hematocrit of 28%.

Patient Characteristics:

Fifty six patients were enrolled in the study, 50 at CSU-ACC and 6 at U Minn. The age, breed, and weight distribution was typical for OS in canine patients. The mean and median age was 7.6 and 8 years respectively with a range of 1.2 to 12. The sex distribution was as follows; 31 male castrated, 22 female spayed and 3 female intact. Breeds most commonly represented included Labrador Retrievers (n=13), Golden Retrievers (n=7), Rottweilers (n=6), and mix breed dogs (n=5). Three dogs represented each of the following breeds; Newfoundland, Great Dane, German Shepherd Dog, and two dogs represented the Saint Bernard and Pyrenees breeds. The remaining 12 dogs were represented by a variety of breeds. The mean and median weight was 43.2 and 41.4 kg respectively with a range of 22.7 to 73.5 kg.

Tumor:

All patients except one had stage IIb OS (disease present outside the periosteum with no detectable metastases based on physical exam and radiographic findings, high grade histologic appearance). One patient had stage IIa (high grade disease confined to the medullar compartment) The right side was affected 25 times and the left was affected 31 times. The front limb was affected 34 times (radius=21, humerous=12, scapula=1) and the hind limb was affected 22 times (femur=11, tibia=11).

Treatment:

Without being bound to theory, the principle of this treatment was based on a 10-day delay of therapy. The rationale for a 10-day delay approach was based on our preclinical data showing that there was statistically significant immunologic protection in animals immunized 10 days before challenge, as well as on the practicality of any delay of therapy approach. The experimental therapy was performed on Day 1, and dogs were followed to assess local and/or systemic toxicity for 10 days. At the end of the investigational period, dogs were treated using standard-of-care for OS.

The treatment sequence was as follows: On Day 0—history, physical, CBC, biochemical profile, urinalysis, chest radiographs, +/− bone scan. On Day 1, lesion biopsy and intratumoral injection. On Days 3, 7, and 10, toxicity monitoring with physical exam, CBC, biochemical profile, urinalysis, lameness evaluation and quality of life assessment. Day 10, amputation of affected limb.

Intratumoral Injection:

Immediately prior to injection of the FasL, core biopsies were done for histopathologic confirmation and to establish primary tumor cultures. Biopsy and injection procedures were done using fluoroscopic radiographic guidance. A 4-inch 8- or 11-gauge Jamshidi needle was used to obtain the tumor biopsies. Patients were anesthetized, prepared and draped for surgery. The Jamshidi needle was advanced through the tumor taking care not to penetrate the opposite cortex. The first sample was taken in the proximal portion of the tumor and a second biopsy was done parallel to the first in the distal portion of the tumor with a minimum of 0.5 cm separating the two sites. Images were recorded to aide in histopathologic orientations after tumor removal.

In an attempt to aid in histologic orientation 0.3 ml of sterile New Methlyene Blue (NMB) was injected into the proximal biopsy tract using an 18 gauge needle. Needle placement was checked using fluoroscopy prior to injection. In the distal biopsy tract, 0.3 ml of FasL was injected using the same technique.

Patients had a light bandage placed over the site and were monitored post operatively for pain or other adverse events. All patients received a non steroidal anti-inflammatory (Deracoxib) and tramadol as needed for pain. The first 5 patients were evaluated for viral shedding and all subsequent patients were returned to their owners that same day.

Histopathologic Evaluation:

The entire tumor specimen from each amputated limb was available for analysis. One ACVP boarded pathologist evaluated and scored all criteria. An HE stained section of each sample was evaluated to confirm tumor diagnosis. Tumor sections were scored for multiple criteria and assigned subjective scores of 0-3 (0=none, 1 to 3 are graded from minimal to abundant). Criteria scored included overall tumor cellularity and the amount of tumor osteoid produced. Tumor sections were also evaluated and subjectively scored for multiple criteria of inflammation including general inflammation, lymphocyte numbers, and neutrophil infiltration. A score for tumor necrosis and tumor associated fibrosis was also assigned. Two pre-treatment OS tumor biopsy samples and 9 OS tissue samples obtained from patients who underwent routine amputation without FasL treatment were used as non-treated comparison and received similar evaluation.

Sample Collection:

Tissue samples were immediately placed in formalin for 24 hrs. Samples were then placed in formic acid based bone decalcifier (1414A, Decal Chemical Corp, Tallman, N.Y.) as needed and was followed by routine processing.

Results

Of 57 patients entered into the study, 54 were evaluated by histopathology and immunohistochemistry with image analysis. Two patients with non-OS tumors were excluded. Two patients with lymph node metastasis were included in the 54 evaluated. For comparison to treated patients, 11 control non-treated OS samples were included and received similar evaluation. Two pre-treatment OS tumor biopsy samples and 9 osteosarcoma tissue samples obtained from patients who underwent routine amputation without FasL treatment were used as a non-treated comparison group.

In general, histopathological evaluation identified a range of tumor cellularity and tumor osteoid matrix in all control and treated samples. Tumor necrosis was present in all samples included in the study (FIG. 1B). More extensive necrosis seemed to be present in sections from treated patients as compared to sections from non-treated OS samples (FIG. 1B). Necrosis was typically associated with some degree of fibrosis (FIG. 1C). More fibrosis was present in the treated subset. There was no apparent correlation between inflammation, necrosis or fibrosis with the tumor cellularity and tumor matrix in either treated or non-treated OS groups (FIG. 1).

Some inflammation was present in all treated OS samples but not all non-treated OS sections (FIG. 1A). Inflammation was predominantly small lymphocytes with some neutrophils admixed. Not all samples having lymphocytes also had neutrophils. Neutrophils were typically within the peripheral areas of tumor necrosis or within the surrounding reactive fibrosis. They were not within areas of viable tumor. Rare samples had few admixed plasma cells. Lymphocytic inflammation was present in areas of necrosis and fibrosis as well as within viable areas of tumor. Two control OSs had marked suppurative inflammation that was predominantly responsible for their high inflammatory score. Control non-treated osteosarcomas had a similar average inflammatory score as did treated OSs. The average lymphocyte score was lower in control OS samples as compared to treated OSs (1.0 vs 1.7). Without being bound to theory, this difference between the inflammatory score and the lymphocyte score may have been due to the admixed influence of neutrophils in the inflammatory score that is not a portion of the lymphocyte score. The non-treated OS subgroup had 2 samples with high inflammatory scores in which the inflammation was characterized as heavy suppurative. No OS from the treated subgroup had similar heavy suppurative inflammation that drove the inflammatory score.

Conclusions

This study demonstrated that FasL therapy promotes inflammation, necrosis, and fibrosis in dogs with spontaneous canine osteosarcoma.

Example 2: FasL-Induced Inflammation Attracts T-Cells into the Tumor

In this example, the tumors of dogs with appendicular OS treated with FasL were examined for extent of lymphocytic infiltration into the tumor.

Methods

Patient selection, treatment, and biological sample preparation were conducted as described in Example 1.

Immunohistochemical Staining:

Immunohistochemical staining was performed by using standard techniques. Briefly, 4-μm sections were cut from formalin fixed-paraffin embedded samples and mounted on positively charged slides. The sections were deparaffinized and then rehydrated with descending alcohol concentrations to buffer. Heat-induced epitope retrieval with citrate buffer, pH 6.0 for 30 minutes was followed by endogenous peroxidase blocking with 3% hydrogen peroxide and incubation with the primary antibody at room temperature for 10 hours.

The primary antibodies used were a polyclonal rabbit anti-human CD3 (A0452, Dako, Carpinteria, Calif.), a monoclonal mouse anti-human Pax-5 (610862, BD Bioscience Pharmigen, San Jose, Calif.), a predituted, dual link polymer HRP secondary antibody (K4061, Dako, Carpinteria, Calif.) and DAB kit (K3467, Dako, Carpinteria, Calif.) were utilized to detect the immunoreactive complexes. The slides then were counterstained with Mayer's hematoxylin.

Image Analysis for CD3:

For each tissue section five images for each stain were taken using a Carl Zeiss Axioplan 2 imaging scope coupled with an AxioCam HRc Carl Zeiss camera. Images were taken at regions of "hotspots" determined after a complete scan of the section. Image analysis was performed using Axio Vision 4.3 software from Carl Zeiss. Briefly, for each image total area of DAB stained nuclei and total area of all nuclei were determined. These were used to determine a % stained cells for each image. Measured values from each of the five images were combined to give single values for each tissue section.

Results

Figure 2:
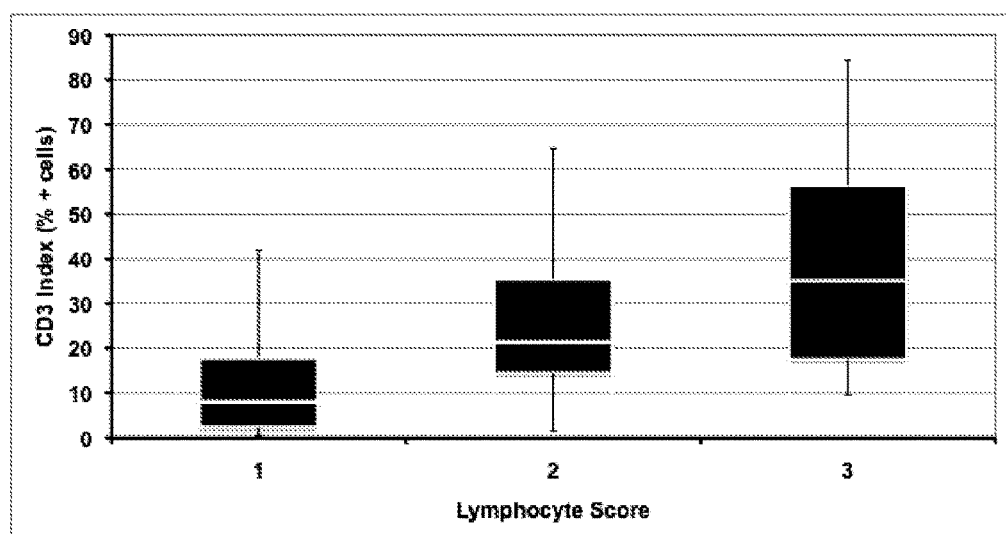
FIG. 2 depicts lymphocyte numbers in the tumors of dogs treated with FasL.
Figure 2:
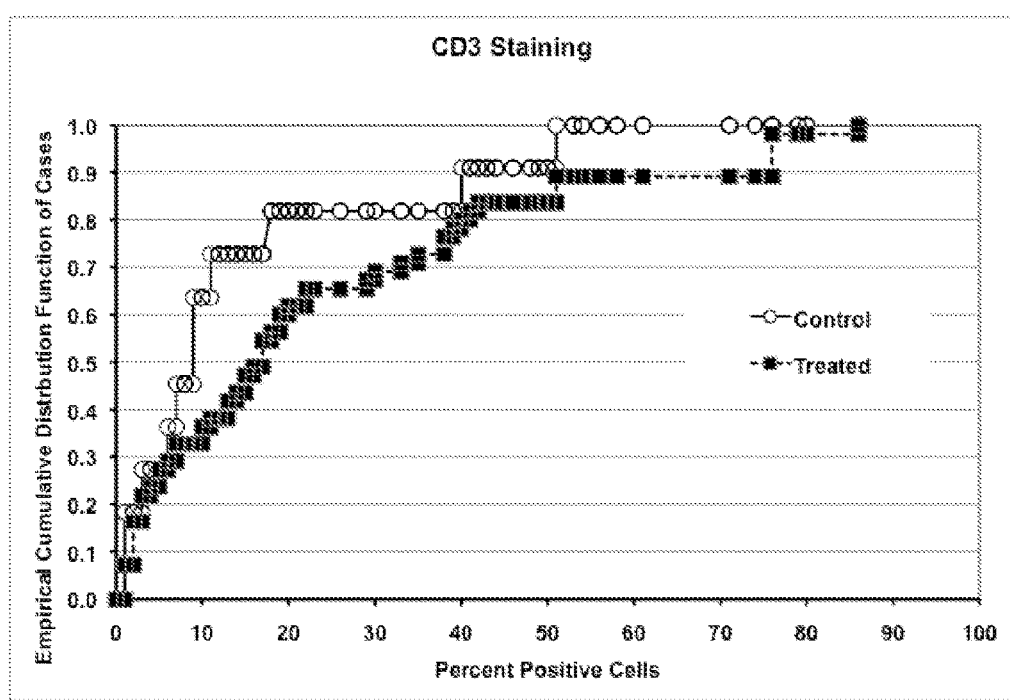

FIG. 2A shows a graph that depicts the empirical cumulative distribution (%) of cases as a function of the proportion of CD3+ cells in the nucleated cells of tumor samples. The median percentage of CD3+ cells in tumors from dogs that received FasL neoadjuvant therapy was 17% (i.e., 17% of the nucleated cell in the tumor cells were T-cells) whereas the median percentage of CD3+ cells in tumors from dogs that did not receive neoadjuvant FasL therapy was 8%.

FIG. 2B demonstrated that there was a positive correlation (R=0.47) between histomorphometric measures of lymphocyte infiltration and the number of CD3+ cells in tumors from dogs that received FasL neoadjuvant therapy. In general, the subjective overall inflammatory score and lymphocyte score paralleled the quantitative CD3 index (FIG. 2B). Some to minimal overlap existed in the CD3 index for the tumors with inflammatory scores of 1 and 2, but tumors with scores of 1 and 3 had no overlap of CD3 indexes (FIG. 2B). There was significant overlap for CD3 indexes in tumors with inflammatory scores of 2 and 3. In all other treated and non-treated samples, lymphocytes were the predominant inflammatory cell and were the cell largely responsible for the inflammatory score assigned. CD3+ T-lymphocytes were the predominant tumor infiltrating lymphocyte with only minor numbers of Pax5+ B-lymphocytes (determined on a subset of treated and non-treated samples).

Conclusion

This study demonstrated that FasL therapy attracts T-cells into the tumor by 10 days following the administration of treatment.

Example 3: FasL Treatment Leads to Tumor Apoptosis

In this example, the tumors of dogs with appendicular OS treated with FasL are examined for extent of cleaved caspase-3 staining within the tumor. When Fas binds to FasL, a Death-Inducing Signaling Complex (DISC) is formed from the trimerization of Fas and the recruitment of several "death domain" proteins to the cytoplasmic region of the Fas protein. The DISC receptor complex is then internalized by the cell's endosomal apparatus which ultimately leads to the cleavage of procaspase-3 into its cleaved and active form. Once activated, caspase-3 helps execute programmed cell death which eventually brings about membrane blebbing, DNA degradation, and other cellular phenomena which are characteristic of apoptosis. However, caspase-3 may also be activated via the intrinsic (a.k.a. mitochondrial) apoptotic pathway. During intrinsic activation, cytochrome c from the mitochondrial inner membrane along with apoptosis-activating factor 1 (Apaf-1), caspase-9, and ATP cleave procaspase-3 into its active form. Therefore, detection of active caspase-3 is indicative of the process of apoptosis actively occurring within a cell, whether the decision to undergo programmed cell death originated externally with a receptor protein such as Fas or internally from within the cell.

Methods

Patient selection, treatment, and biological sample preparation were conducted as described in Example 1.

Immunohistochemical Staining:

Immunohistochemical staining was performed by using standard techniques. Briefly, 4-µm sections were cut from formalin fixed-paraffin embedded samples and mounted on positively charged slides. The sections were deparaffinized and then rehydrated with descending alcohol concentrations to buffer. Heat-induced epitope retrieval with EDTA buffer, pH 8.0 for 30 minutes was followed by endogenous peroxidase blocking with 3% hydrogen peroxide and incubation with the primary antibody at room temperature for 10 hours.

The primary antibodies used were a polyclonal rabbit anti-human caspase-3 active (AF835, RnD Systems, Minneapolis, Minn.) a prediluted, dual link polymer HRP secondary antibody (K4061, Dako, Carpinteria, Calif.). A DAB kit (K3467, Dako, Carpinteria, Calif.) was utilized to detect the immunoreactive complexes. The slides then were counterstained with Mayer's hematoxylin.

Results

Figure 3:
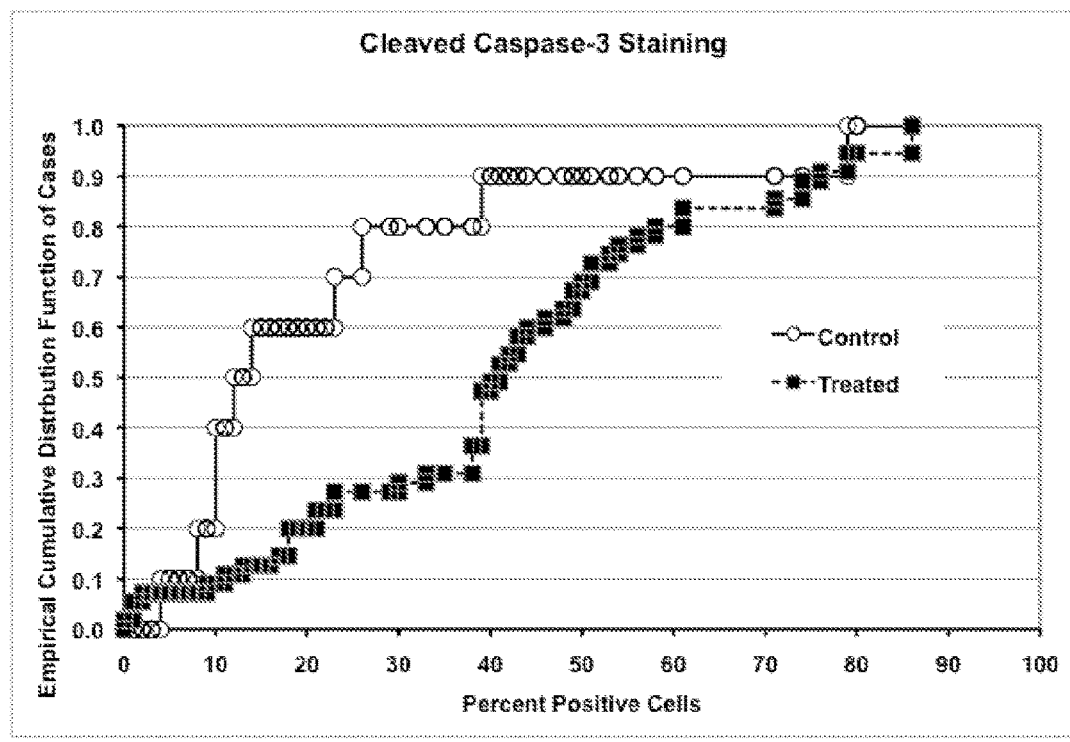
FIG. 3 depicts the empirical cumulative distribution of cleaved caspase-3 in tumors from control dogs and dogs that received FasL therapy.

FIG. 3 shows a graph depicting the empirical cumulative distribution (%) of cases as a function of the proportion of cells with evidence of cleaved caspase-3 in the nucleated cells of each tumor. The median percentage of cells with cleaved caspase-3 in tumors from dogs that received neoadjuvant FasL therapy was 41% (i.e. 41% of the nucleated cells in the tumor showed evidence of apoptosis), whereas the median percentage of cells with detectable cleaved caspase-3 in tumors from dogs that did not receive neoadjuvant therapy was 14%.

Necrosis score and caspase-3 active indexes had no apparent correlation. While apoptosis can be one method of necrosis, HE evaluation suggests that coagulative necrosis is the dominant type of necrosis in some tumor samples. Likewise, many samples had large regions of replacement fibrosis where originally tumor had been present. In these areas, no active necrosis (apoptosis or other) was identified. Without being bound to theory, high subjective necrosis score and low caspase index could be an issue of chronicity in that necrosis/apoptosis had already occurred and was cleared at the time of amputation.

Conclusions

This study demonstrated that FasL therapy leads to caspase-3-mediated programmed cell death.

Example 4: Inflammation Induced by FasL Neoadjuvant Therapy is Associated with Improved Survival of Dogs with Osteosarcoma This example examined survival data from a cohort of 57 dogs treated with FasL as a neoadjuvant to standard of care with naturally occurring appendicular osteosarcoma.

Methods

Patient selection, treatment, and biological sample preparation were conducted as described in Example 1. Fifty seven dogs were enrolled in the study. Two dogs were diagnosed with intramedullary tumors that were not OS, two dogs were withdrawn from the study, two dogs had pre-existing metastasis, two were lost to follow up, and four died of other causes. The rest of the patients were followed until their death, which was then determined to be disease-related ("died of disease") or unrelated to disease recurrence ("died of other causes").

Results

Table 1 depicts disease free interval (DFI), overall survival (OS), and percentage of dogs alive at 200 days following treatment and amputation that were treated with standard of care (carboplatin (carbo) control) and treated with FasL. Additionally, the disease free interval and overall survival of those dogs which had inflammation scores of 1 (low inflammation) as determined by histopathologic evaluation (see Example 1) or inflammation scores of 2-3 (moderate to high inflammation) is depicted. As a single group, eligible dogs in the FasL group are no different that dogs in the Carbo control group for DFI and overall survival. However, as also indicated in Table 1, dogs with inflammation scores of 2 or 3 have significantly improved survival compared to dogs with inflammation scores of 1 or the Carbo control dogs (p<0.05).

TABLE 1

Survival data based on treatment and histopathologic evaluation of inflammation.

| Group | Disease Free Interval | Overall Survival | % Alive at 200 Days |
|---|---|---|---|
| Carbo control | 213 | 231 | 56 |
| All FasL | 209 | 240 | 65 |
| Inflammation Score = 1 | 177 | 198 | 46 |
| Inflammation Score = 2/3 | 292 | 360 | 86 |

Figure 4:
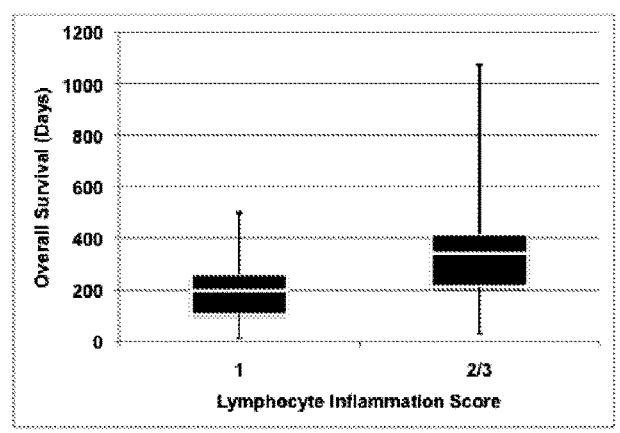
FIG. 4A depicts overall survival of dogs versus inflammation as measured by lymphocyte inflammation score.
FIG. 4B-C depicts Kaplan-Meier analyses of disease free interval (DFI.
Figure 4:
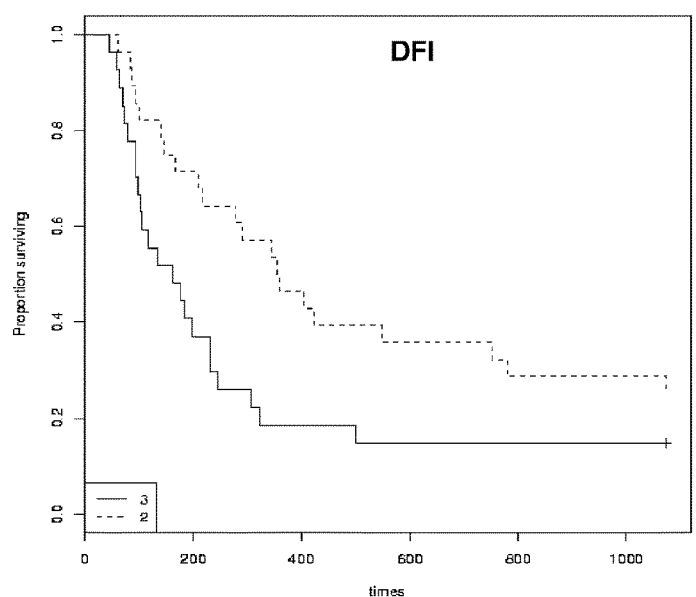
Figure 4:
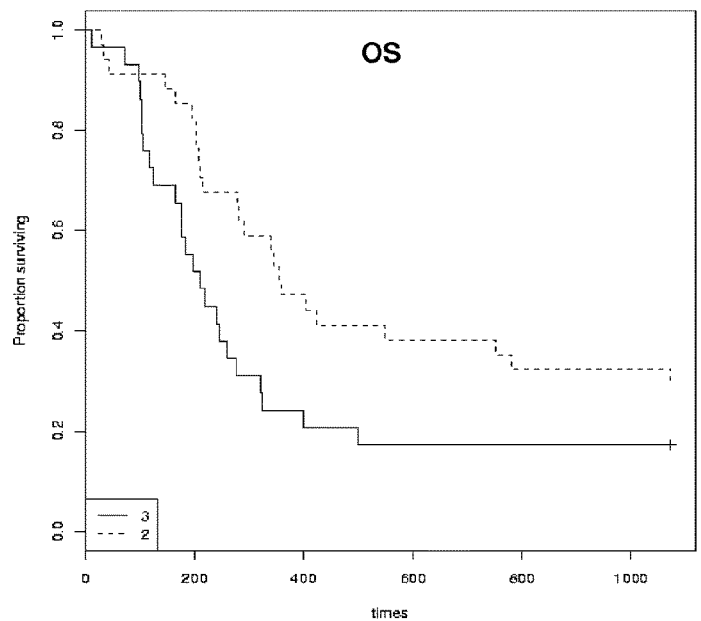

This is also demonstrated in FIG. 4A which shows a graph depicting survival as a function of inflammatory scores. Dogs with inflammation scores of 2 or 3 show longer median overall survival (360 days) than dogs with scores of 1 (198 days). FIGS. 4B-C depict a Kaplan-Meier analysis of disease free interval (FIG. 4B) and overall survival (FIG. 4C) of dogs treated with neoadjuvant FasL that had inflammatory scores of 1 (group 3, FIGS. 4B-C) versus dogs that had inflammatory scores of 2 or 3 (group 2, FIGS. 4B-C). The data from the Kaplan-Meier analyses was statistically significant as determined by log rank analysis (p<0.05).

Figure 5:
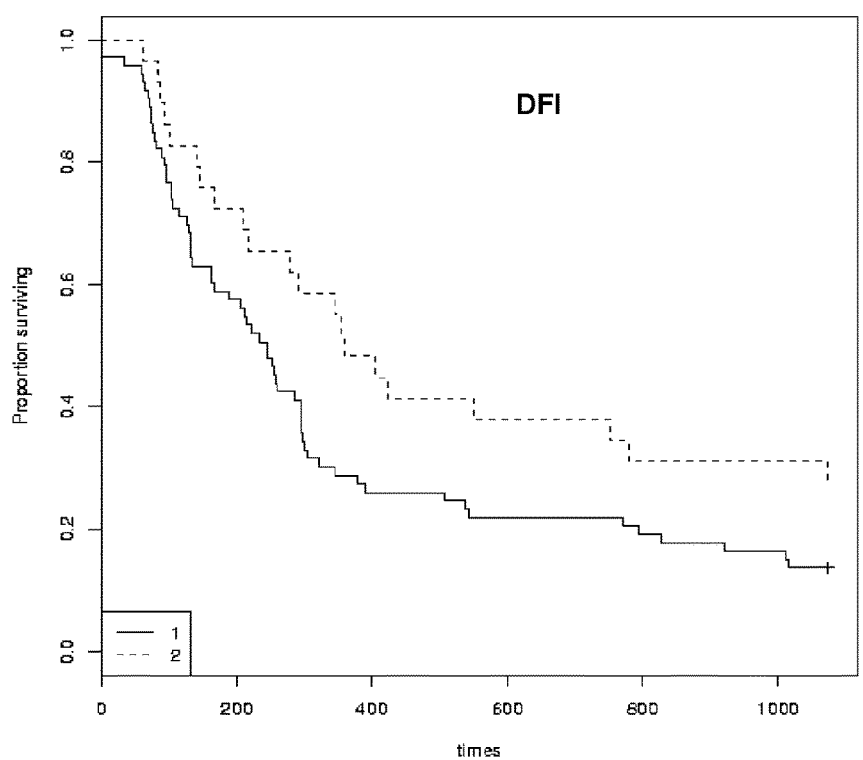
FIG. 5 depicts a Kaplan-Meier analysis of disease free interval (DFI.
Figure 5:
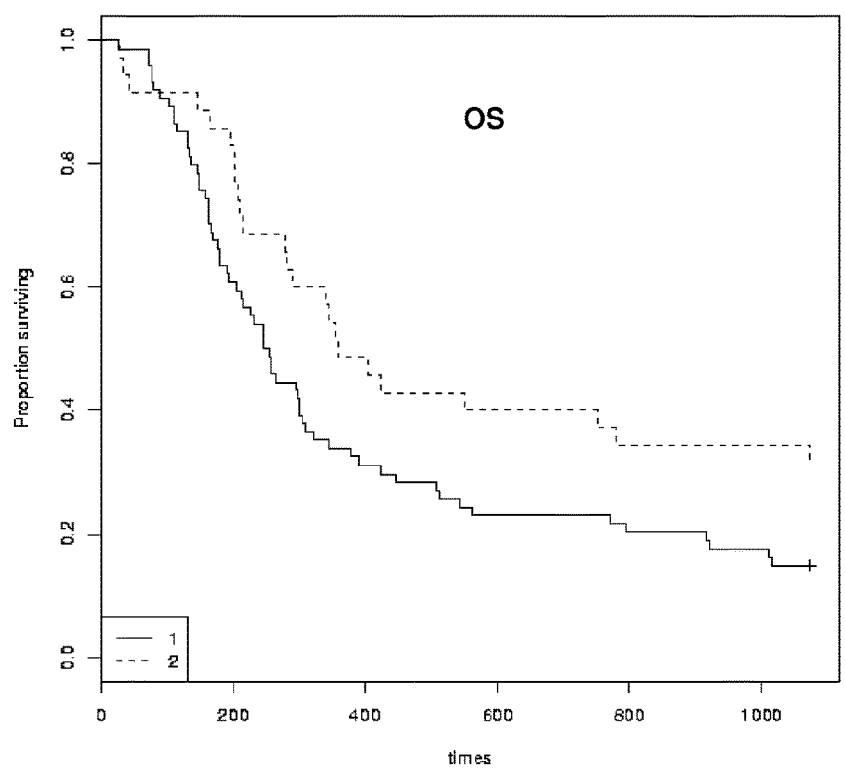
Figure 6:
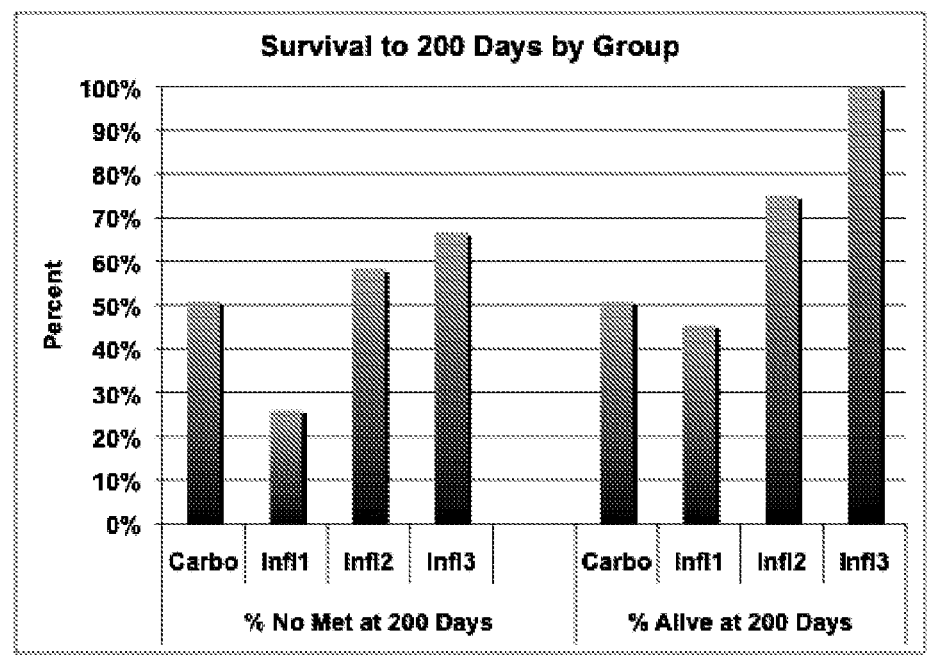
FIG. 6A depicts disease free interval in dogs treated with the standard of care versus dogs treated with the standard of care plus FasL with the data stratified according to inflammation score.
FIG. 6B depicts a Kaplan-Meier analysis of overall survival of dogs treated with FasL according to inflammation scores.
Figure 6:
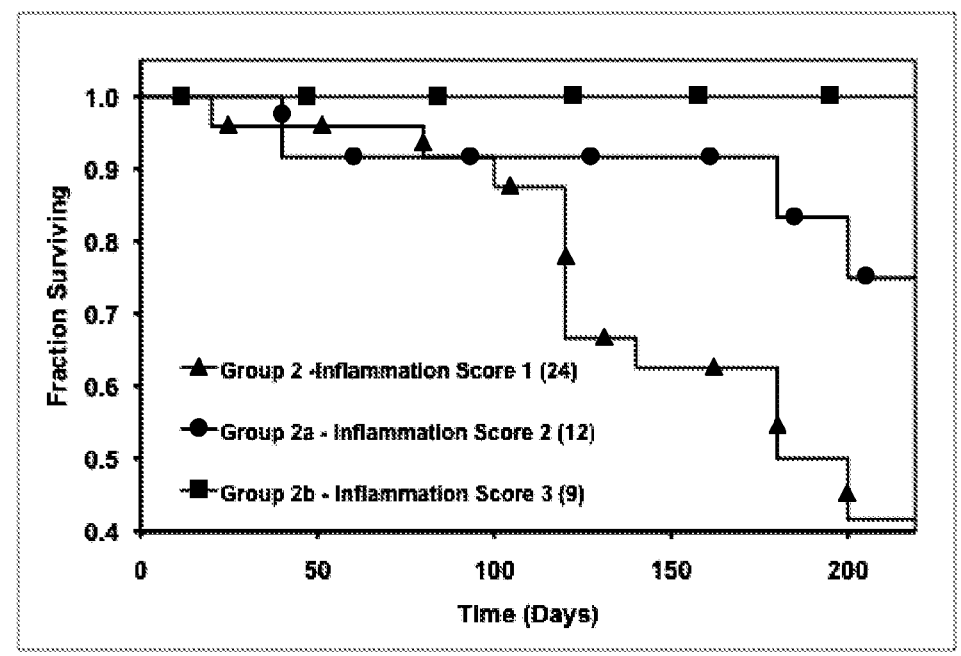

The data shown in FIG. 5 also demonstrated that inflammation induced by FasL neoadjuvant therapy was associated with improved survival of dogs with osteosarcoma. A Kaplan-Meier analysis of disease free interval (FIG. 5A) and overall survival (FIG. 5B) of dogs treated with neoadjuvant FasL that had inflammatory scores of 2 or 3 (group 2, FIGS. 5A-B) versus a contemporary Carbo control cohort treated with the same standard of care (group 1, FIGS. 5A-B) is depicted in FIG. 5. The data from this Kaplan-Meier analysis was also statistically significant as determined by log rank analysis (p<0.05). The data depicted in FIG. 6 further shows that FasL neoadjuvant therapy-induced inflammation was associated with improved survival. FIG. 6A demonstrated disease free interval and survival in dogs treated with Carbo standard of care or with standard of care plus neoadjuvant FasL stratified according to inflammation scores while FIG. 6B shows a graph depicting a Kaplan-Meier analysis of overall survival of dogs according to their inflammation scores as graded by histopathologic evaluation.

Conclusions

This study demonstrated that survival improvement was apparent in dogs with greater inflammation or lymphocyte infiltration who were in the top $50^{th}$ percentile of apoptosis whereas it was no different than standard of care alone in dogs with lower inflammation scores and who were in the bottom $50^{th}$ percentile of apoptosis.

Example 5: Reduced Fas Expression in Tumor Cells is a Variable Associated with Prognostically Advantageous Inflammation Given that survival improvement was observed in dogs with higher amounts of inflammation and tumoral lymphocyte infiltration following treatment with adenoviral FasL, it was hypothesized that the level of Fas expression may vary within the tumors of dogs with appendicular OS. This study examined expression of Fas in tumors and the association of Fas expression with inflammation score and survival outcome.

Methods

Patient selection, treatment, and biological sample preparation were conducted as described in Example 1.

Total RNA was extracted from the tumors of dogs treated with FasL and which exhibited either low or moderate to high levels of inflammation. Total extracted RNA was reverse transcribed into cDNA with reverse transcriptase and then total cDNA was diluted to 950 ng/μL. The qRT-PCR reaction for measurement of Fas expression was set up using 10 μL SYBER green (FastStart SYBR Green Master, Roche Diagnostics, Hoffmann-La Roche, Basel, Switzerland), 0.5 μL forward and reverse primers (Forward: 5'-TGTAGCT-CATCCTCCGGTGT-3'; Reverse: 5'-GACGAAAGC-CCAAAGAGTCA-3'), 5.5 μL RNase water, and 4 μL cDNA (for a total of 50 ng cDNA) in 1× sample buffer. qRT-PCR was run over the course of 40 cycles for Fas using an Eppendorf RealPlex2 Master Cycler (Hamburg, Germany) with the following cycling parameters: denaturing at 95° C. for 0:15 seconds, annealing at 57° C. for 0:30 seconds, and extension at 68° C. for 0:30 seconds. Melting curve analysis was conducted starting at 60° C. for 0:15 seconds ramping up to 95° C. over 20 minutes. Samples were stored at 4° C. in the instrument until analysis was complete and verification of amplification products was conducted as needed. Fas expression was normalized to the expression of the housekeeping gene glyceraldehyde 3-phosphate dehydrogenase (GAPDH) which was run over the course of 12 cycles (Forward: 5'-GGAGTCCACTGGCGTCTTCAC-3'; Reverse: 5'-GAGGCATTGCTGATGATCTTGAGG-3'). Normalized values for Fas expression of all samples evaluated were then numerically rank ordered by score and the median score was assigned a calibration score of "1." The normalized qRT-PCR values from all other samples tested were then calibrated to that of this median value to obtain calibration scores for each sample tested by dividing the median normalized qRT-PCR calibration value by the normalized qRT-PCR value of each individual sample.

Results

Figure 7:
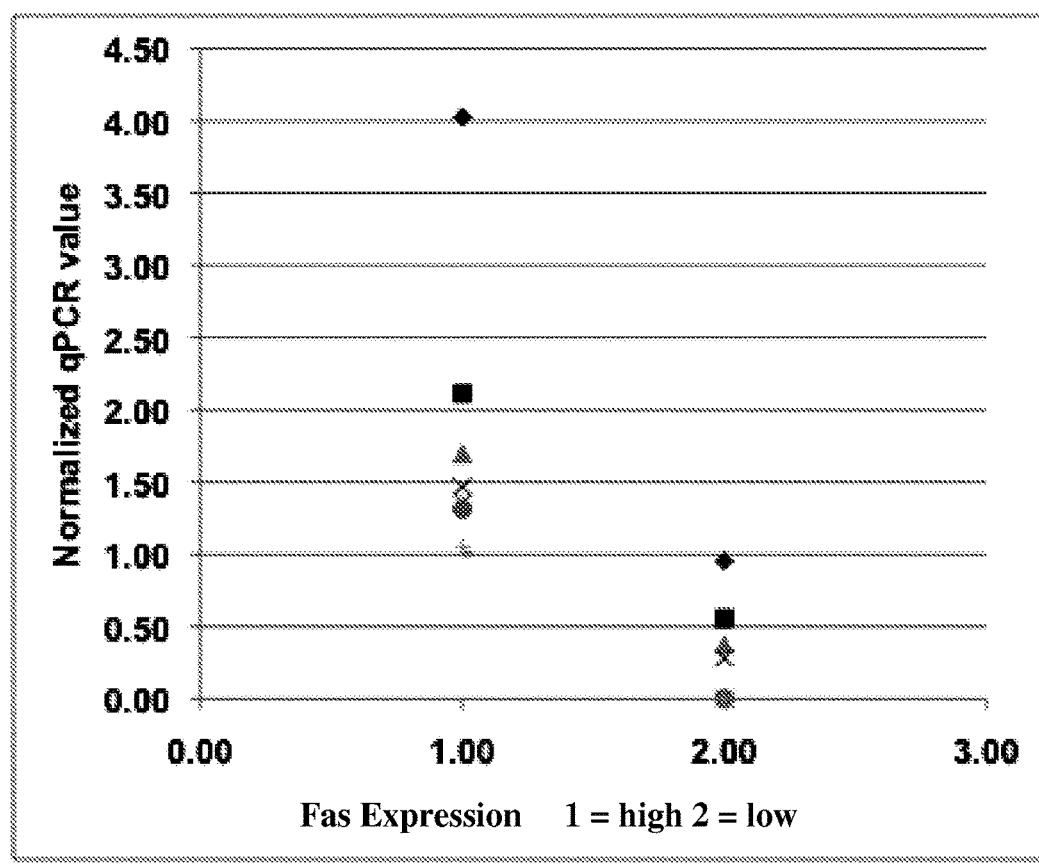
FIG. 7 depicts expression of Fas from individual dogs grouped by membership in either high Fas expressing (Fas high) or low Fas expressing (Fas low) groups.

Dogs whose tumors had a calibrated Fas expression score of one or greater were placed in a "Fas-Hi' group while dogs with Fas expression scores less than one were designated "Fas-Low." These results are shown in Table 2 and illustrated graphically in FIG. 7.

TABLE 2

Calibrated Fas expression data separated by group

| "Fas-High" | "Fas-Low" |
|---|---|
| 4.03 | 0.953 |
| 2.11 | 0.555 |

TABLE 2-continued

Calibrated Fas expression data separated by group

| "Fas-High" | "Fas-Low" |
|---|---|
| 1.69 | 0.374 |
| 1.46 | 0.281 |
| 1.36 | 0.004 |
| 1.31 | 0.003 |
| 1.05 | 0.001 |
| 1.00 | |

Figure 8:
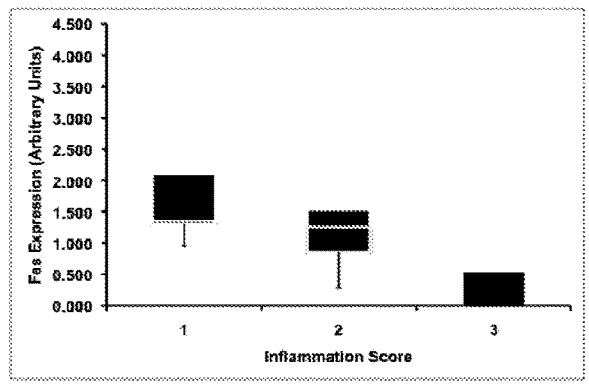
FIG. 8A depicts Fas expression in tumors classified by histomorphometric measures of inflammation.
FIG. 8B depicts disease free interval in dogs that received FasL therapy with low Fas expressing tumors (solid) or high Fas expressing tumors (dashed) (p=0.06).
FIG. 8C depicts overall survival in dogs that received FasL therapy with low Fas expressing tumors (solid) or high Fas expressing tumors (dashed) (p=0.06).
FIG. 8D depicts the number of dogs with no detectable metastasis and that were alive 200 days from either the low Fas expressing or high Fas expressing tumor groups.
Figure 8:
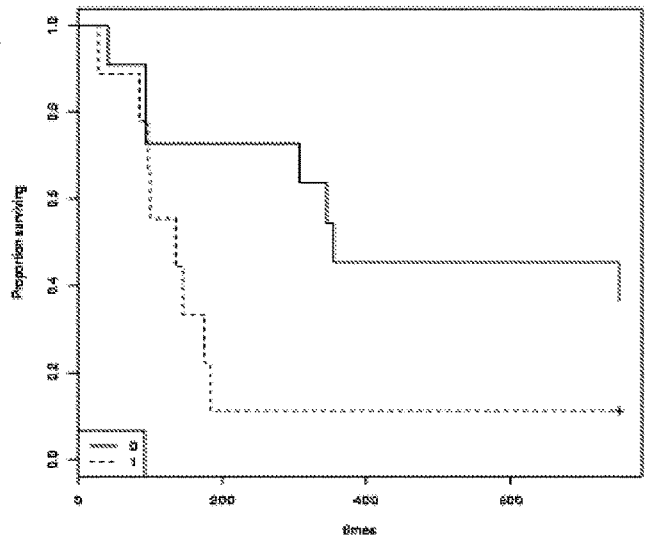
Figure 8:
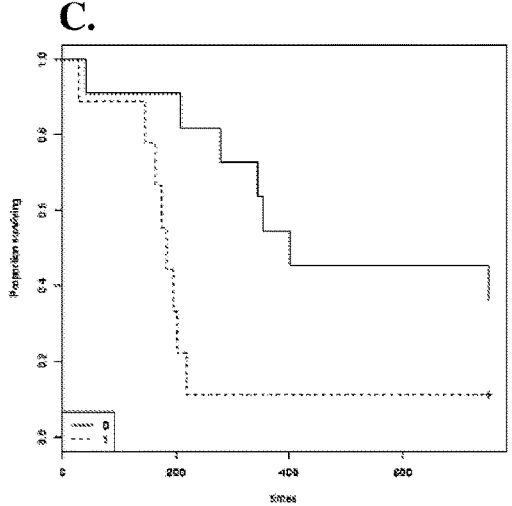
Figure 8:
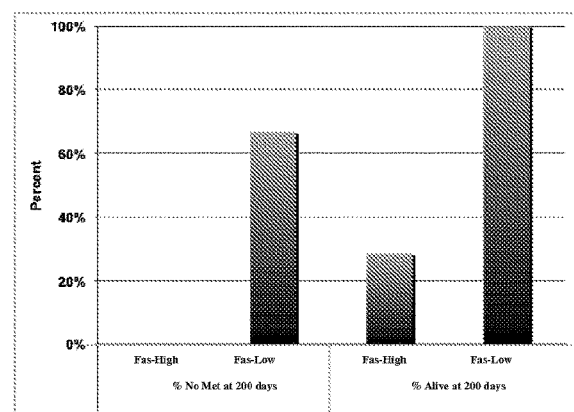

The data shown in FIG. 8A demonstrated that inverse correlation between Fas expression measured by qRT-PCR and the histomorphometric measures of inflammation described in Example 1. Increased inflammation was seen to be associated with lower levels of Fas expression. The data in FIGS. 8B and C illustrated disease-free interval (FIG. 8B) and overall survival (FIG. 8C) in dogs that received neoadjuvant FasL therapy with "Fas Low" (solid line) or "Fas high" (dashed line) tumors (p=0.01). The data in FIG. 8D demonstrated the proportion of dogs that had not detectable metastasis and that were alive, respectively, at 200 days from each of the "Fas Low" or "Fas high" groups.

Conclusions

Reduced Fas expression in tumor cells was a variable associated with prognostically advantageous inflammation and this relationship was not observed in dogs that did not receive FasL therapy (see Example 4). Together, these data suggested that FasL gene therapy can improve survival in naturally occurring tumors of large animals and may be most effective when tumors fail to express Fas receptor, thus permitting FasL to exert its pro-inflammatory effects on the tumor microenvironment.

Example 6: Correlation Between Fas mRNA Expression in Cultured Cells and Fas Protein Expression in Tissue Sections of Canine Osteosarcoma Samples This example utilizes immunohistochemistry (IHC) to correlate Fas mRNA expression as determined by qRT-PCR with Fas protein expression in tissues.

Methods

Isolation of RNA from Tumors:

0.1 cm$^3$ canine osteosarcoma tumor sections from 8 separate samples were disaggregated to single cell suspensions, stromal elements were removed by running the cells through sequential mesh filters, and cells were cultured for 3 passages before cryopreservation. This method resulted in enriched populations of osteosarcoma cells (Thomas et al., 2005, *Genome Res* 15:1831-1837).

qRT-PCR:

RNA was isolated from cryopreserved cells and quantitative real time PCR was done using routine methods as described (Scott et al., 2011, *Bone* 49:356-367). Data are shown as the ΔΔCT, where the cycle time (CT) for Fas mRNA was subtracted from the CT for the housekeeping gene GAPDH, yielding a number that represented a $\log_2$ function of expression, converted to a ratio using the formula $\frac{1}{2}^N$. When using qRT-PCR from cultured cells or from fine needle aspirate samples of a tumor, in the case of canine osteosarcoma as an example, a sample with a Fas mRNA ΔΔCT>5×10$^{-5}$ is considered "high" and a sample with a Fas mRNA ΔΔCT<5×10$^{-5}$ is considered "low". The Fas mRNA MCT is calculated as the CT for Fas mRNA subtracted from the CT for GAPDH, and yielding a number that represents a $\log_2$ function of expression, which is converted to a ratio using the formula $\frac{1}{2}^N$. In the application of this test as a biomarker, a "high" Fas sample and a "low" Fas sample for the same tissue type must be included to calibrate the test every time it is performed.

Quantitation of Fas Protein Expression Using IHC:

Tissue sections that contained sufficient material for evaluation were stained using an anti-Fas antibody validated for recognition of canine Fas using immunoblotting and IHC on lymph node sections. Scoring was done by an experienced blinded operator using a semiquantitative scale from 0 to 4+ where 0 was no different from the background in the section and 4+ was equivalent to staining in leukocytes (neutrophils) for each section. When using IHC, a semiquantitative score is defined by convention from 0 to 4+ where 0 shows staining that is no different from the background in the section and 4+ shows staining that is equivalent to leukocytes (neutrophils) in the section. Neutrophils can be found in virtually any tissue section (within or outside blood vessels), within the tumor, or in adjacent normal tissue. In an automated setting, a control can be included in the same slide during processing. The scoring also can be automated to assess optical density of the stain using a system such as the Aperio™; however, care must be taken to prevent misinterpretation of artificially increased density in tissue folds or in condensed cells. In the case of canine osteosarcoma as an example, a sample with consistent expression of Fas in every cell and where the maximal score is considered "high" and a sample where at least a subset of the tumor cells show no expression of Fas (score=0) and where the maximal score is <2 is considered "low." In the application of this test as a biomarker, a "high" Fas sample and a "low" Fas sample for the same tissue type must be included to calibrate the test every time it is performed.

Results

For quantitation using IHC, leukocytes were found to be present in every section, allowing for consistent scoring. One sample was done in duplicate and yielded the same results. All samples showed variability of Fas expression and data are shown in Table 3 as the range of staining in tumor cells. There was a positive trend for direct correlation between cultured cells that had a Fas mRNA ΔΔCT>5×10$^{-5}$ ("high") and tissue sections were all tumor cells stained positive and included cells with 2+ expression and cultured cells that had a Fas mRNA ΔΔCT<5×10$^{-5}$ ("low") and tissue sections were at least some of the tumor cells stained negative. Only one sample (308506) showed a discrepancy where Fas mRNA was "high" and no Fas protein was detectable in tumor cells by IHC.

TABLE 3

Correlation between Fas mRNA expression in cultured cells and Fas protein expression in tissue sections of canine osteosarcoma samples

| Case ID | Fas mRNA (qRT-PCR in cultured cells, ΔΔCT with GAPDH × 10$^{-5}$) | Fas protein (IHC in tissue sections, 0-4+) |
|---|---|---|
| 252019 | 1.38 (Fas low) | 0 (Fas low) |
| 161366 | 6.41 (Fas high) | 2+ to 3+ (Fas high) |
| 322895 | 4.90 (Fas low) | 0 to 1+ (Fas low) |
| 330774 | 6.63 (Fas high) | 2+ to 3+ (Fas high) |
| 272429 | 1.83 (Fas low) | 0 to 1+ (Fas low) |
| 253012 | 2.71 (Fas low) | 0 to 2+ (Fas low) |
| 308506 | 10.3 (Fas high) | 0 (Fas low) |
| 238987 | 19.7 (Fas high) | 1+ to 2+ (Fas high) |

Conclusions

This study demonstrated that IHC can be used to assess levels of Fas protein expression in tissue sections from tumors. The assessed level of Fas protein expression correlates with the observed level of Fas mRNA expression in cultured cells derived from the same tumor.

What is claimed is:

1. A method of treating osteosarcoma in an individual, comprising administering an effective amount of a composition comprising FasL or a composition comprising a vector encoding FasL to the osteosarcoma tumor, wherein the individual has low Fas expression in the cells of the osteosarcoma tumor, and wherein the administration of the composition reduces osteosarcoma metastasis.

2. The method of claim 1, wherein the vector encoding FasL is an adenoviral vector encoding FasL.

3. A method for inducing lymphocyte infiltration in an individual having osteosarcoma tumor, comprising administering an effective amount of a composition comprising FasL or a composition comprising a vector encoding FasL to the tumor, wherein the individual has low Fas expression in the cells of the osteosarcoma tumor, and wherein the administration of the composition increases lymphocyte infiltration into the osteosarcoma tumor.

4. The method of claim 3, wherein the vector encoding FasL is an adenoviral vector encoding FasL.

* * * * *